(12) United States Patent
Bombrun et al.

(10) Patent No.: US 6,462,047 B1
(45) Date of Patent: *Oct. 8, 2002

(54) CARBOLINE DERIVATIVES AS CGMP PHOSPHODIESTERASE INHIBITORS

(75) Inventors: Agnes Bombrun, Monnetier Mornex; Françoise Gellibert, Paris Cedex, both of (FR)

(73) Assignee: ICOS Corporation, Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/744,859

(22) PCT Filed: Sep. 16, 1998

(86) PCT No.: PCT/EP98/06050

§ 371 (c)(1),
(2), (4) Date: May 16, 2001

(87) PCT Pub. No.: WO00/15639

PCT Pub. Date: Mar. 23, 2000

(51) Int. Cl.⁷ .................. A61K 31/437; A61K 31/496; A61K 31/506; C07D 471/04; C07D 239/02; C07D 401/14
(52) U.S. Cl. .................. 514/253.03; 514/252.18; 514/256; 514/275; 514/292; 544/332; 544/335; 544/361; 546/85
(58) Field of Search ............... 514/292, 256, 514/275, 253.03, 252.18; 546/85; 544/361, 332, 335

(56) References Cited

U.S. PATENT DOCUMENTS 6,117,881 A * 9/2000 Bombrun .................. 514/292

FOREIGN PATENT DOCUMENTS

| WO | WO 96/32003 | * 10/1996 |
| WO | WO 97/43287 | * 11/1997 |

OTHER PUBLICATIONS

King FD. Medicinal Chemistry. Principles and Practice. The Royal Society of Chemistry. 1994. pp. 206–209.*

* cited by examiner

*Primary Examiner*—Evelyn Mei Huang
(74) *Attorney, Agent, or Firm*—Marshall, Gerstein & Borun.

(57) ABSTRACT

Compounds of general structural formula (I) wherein A represents a 5- or 6-membered heteroaryl group containing at least one heteroatom selected from the group consisting of oxygen, nitrogen, and sulfur, and use of the compounds, and salts and solvates thereof, as therapeutic agents, are disclosed.

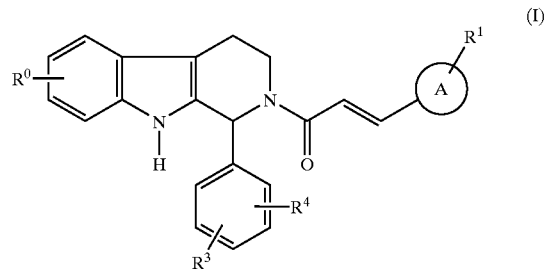

22 Claims, No Drawings

CARBOLINE DERIVATIVES AS CGMP PHOSPHODIESTERASE INHIBITORS

This application is a 371 of PCT/ET98/06050 filed Sep. 16, 1998.

FIELD AND BACKGROUND OF THE INVENTION

This invention relates to a series of carboline derivatives, to processes for their preparation, to pharmaceutical compositions containing them, and to their use as therapeutic agents. In particular, the invention relates to carboline derivatives which are potent and selective inhibitors of cyclic guanosine 3', 5'-monophosphate specific phosphodiesterase (cGMP-specific PDE), and in particular PDE5, and have utility in a variety of therapeutic areas where such inhibition is considered beneficial, including the treatment of cardiovascular disorders and erectile dysfunction.

SUMMARY OF THE INVENTION

The present invention provides compounds represented by formula (I):

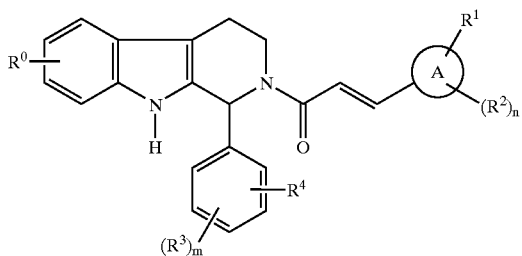

(I)

wherein
A represents a 5- or 6-membered heteroaryl group containing at least one heteroatom selected from the group consisting of oxygen, nitrogen, and sulphur;
$R^0$ represents hydrogen or halogen;
$R^1$ is selected from the group consisting of
hydrogen,
nitro ($NO_2$),
trifluoromethyl,
trifluoromethoxy,
halogen,
cyano (CN),
a 5- or 6-membered heterocyclic group containing at least one heteroatom selected from the group consisting of oxygen, nitrogen, and sulphur, optionally substituted with $C(=O)OR^a$ or $C_{1-4}$alkyl,
$C_{1-6}$alkyl, optionally substituted with $OR^a$,
$C_{1-3}$alkoxy,
$C(=O)R^a$,
$O—C(=O)R^a$,
$C(=O)OR^a$,
$C_{1-4}$alkyleneHet,
$C_{1-4}$alkyleneC(=O)OR^a$,
$O—C_{1-4}$alkylene-C(=O)OR^a$,
$C_{1-4}$alkylene-O—$C_{1-4}$alkylene-C(=O)OR^a$,
$C(=O)NR^aSO_2R^c$,
$C(=O) C_{1-4}$alkyleneHet,
$C_{1-4}$alkylene $NR^aR^b$,
$C_{2-6}$alkenyleneNR^aR^b$,
$C(=O)NR^aR^b$,
$C(=O)NR^aR^c$,
$C(=O)NR^aC_{1-4}$alkyleneOR^b$,
$C(=O)NR^aC_{1-4}$alkyleneHet,
$OR^a$,
$OC_{2-4}$alkylene $NR^aR^b$,
$OC_{1-4}$alkylene-CH($OR^a$)$CH_2$—$NR^aR^b$,
$O—C_{1-4}$alkyleneHet,
$O—C_{2-4}$alkylene-$OR^a$,
$O—C_{2-4}$alkylene-$NR^a$—C(=O)—$OR^b$,
$NR^aR^b$,
$NR^aC_{1-4}$alkyleneNR^aR^b$,
$NR^aC(=O)R^b$,
$NR^aC(=O)NR^aR^b$,
$N(SO_2C_{1-4}$alkyl)$_2$,
$NR^a(SO_2C_{1-4}$alkyl),
$SO_2NR^aR^b$,
and $OSO_2$trifluoromethyl;
$R^2$ is selected from the group consisting of hydrogen, halogen, $OR^a$, $C_{1-6}$alkyl, $NO_2$, and $NR^aR^b$;
or $R^1$ and $R^2$ are taken together to form a 3- or 4-membered alkylene or alkenylene chain component of a 5- or 6-membered ring, optionally containing at least one heteroatom;
$R^3$ is selected from the group consisting of hydrogen, halogen, $NO_2$, trifluoromethoxy, $C_{1-6}$alkyl, $OC_{1-6}$alkyl, and $C(=O)OR^a$;
$R^4$ is hydrogen,
or $R^3$ and $R^4$ are taken together to form a 3- or 4-membered alkylene or alkenylene chain component of a 5- or 6-membered ring, optionally containing at least one heteroatom;
Het represents a 5- or 6-membered heterocyclic group containing at least one heteroatom selected from the group consisting of oxygen, nitrogen, and sulfur, and is optionally substituted with $C_{1-4}$alkyl;
$R^a$ and $R^b$ can be the same or different, and are independently selected from hydrogen and $C_{1-6}$alkyl;
$R^c$ represents phenyl or $C_{4-6}$cycloalkyl, wherein the phenyl or $C_{4-6}$ cycloalkyl can be optionally substituted with one or more halogen atoms, one or more $C(=O)OR^a$, or one or more $OR^a$;
n is an integer 1, 2, or 3;
m is an integer 1 or 2;
and pharmaceutically acceptable salts and solvates (e.g., hydrates) thereof.

In a preferred embodiment, $R^2$ is hydrogen, n and m are the integer 1, and the compounds are represented by the formula (II):

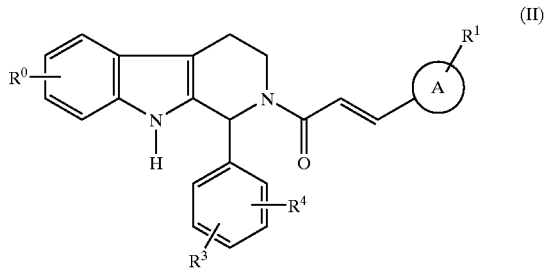

(II)

wherein
A represents a 5- or 6-membered heteroaryl group containing at least one heteroatom selected from the group consisting of oxygen, nitrogen, and sulphur;

$R^0$, $R^4$, $R^a$, $R^b$, $R^c$, and Het are as defined above;
$R^1$ is selected from the group consisting of
  hydrogen,
  $NO_2$,
  halogen,
  CN,
  a 5- or 6-membered heterocyclic group containing at least one heteroatom selected from the group consisting of oxygen, nitrogen, and sulphur, optionally substituted with $C(=O)OR^a$ or $C_{1-4}$alkyl,
  $C_{1-6}$alkyl optionally substituted with $OR^a$,
  $C_{1-3}$alkoxy,
  $C(=O)OR^a$,
  $C_{1-4}$alkyleneHet,
  $O-C_{1-4}$alkylene-$C(=O)OR^a$,
  $C_{1-4}$alkyleneNR$^a$R$^b$,
  $C(=O)NR^aR^b$,
  $C(=O)NR^aR^c$,
  $OR^a$,
  $OC_{2-4}$alkyleneNR$^a$R$^b$,
  $O-C_{1-4}$alkyleneHet,
  $NR^aR^b$,
  and $NR^aC_{1-4}$alkyleneNR$^a$R$^b$;
$R^3$ is selected from the group consisting of hydrogen and $OCH_3$;
$R^4$ is hydrogen,
or $R^3$ and $R^4$ together form a 3- or 4-membered alkylene or alkenylene chain component of a 5- or 6-membered ring, optionally containing at least one heteroatom;
and pharmaceutically acceptable salts and solvates (e.g., hydrates) thereof.

The term alkyl or alkylene as used herein contains the indicated number of carbon atoms and includes straight chained and branched alkyl or alkylene groups, typically methyl, methylene, ethyl, ethylene, and straight chain and branched propyl, propylene, butyl, and butylene groups. The term alkenylene as used herein contains the indicated number of carbon atoms and includes straight chained and branched alkenylene groups, like ethyenylene.

The term halogen as used herein includes fluorine, bromine, chlorine, and iodine groups.

The term 5- or 6-membered heteroaryl group as used herein includes, for example, thiophene, furan, pyrrole, imidazole, pyrimidine, and pyridine.

The term 5- or 6-membered heterocyclic group as used herein includes 5- or 6-membered heterocycloalkyl and heteroaryl groups, e.g., morpholinyl, piperidyl, pyrrolidinyl, or piperazinyl.

Preferably A is a thiophenyl, furyl, pyrimidinyl, pyridyl, or imidazolyl group. Most preferably, A represents a pyridyl group.

When A represents a thiophenyl group, $R^1$ preferably is selected from a group consisting of hydrogen, $NO_2$, $C_{1-4}$alkyleneNR$^a$R$^b$, e.g., $CH_2NMe_2$, and $C_{1-4}$alkyleneHet, wherein Het is optionally substituted by $C_{1-4}$alkyl, e.g., a pyrrolidinylmethyl or N-methyl piperazinylmethyl group. Me is an abbreviation for methyl, i.e., $CH_3$.

When A represents a furyl group, $R^1$ preferably is hydrogen or $C_{1-4}$alkyleneNR$^a$R$^b$, e.g., $CH_2NMe_2$.

When A represents a pyrimidine group, $R^1$ preferably is hydrogen or $NH_2$.

When A represents a pyridine group, $R^1$ preferably represents hydrogen, a 5- or 6-membered heterocyclic group containing at least one heteroatom selected from the group consisting of oxygen, nitrogen, and sulphur, optionally substituted by $C_{1-4}$alkyl, e.g., N-methyl imidazole, N-methyl piperazine, or pyrrolidine, $C(=O)OR^a$, e.g., $CO_2H$ or $CO_2Me$, $C_{1-4}$alkyleneHet, wherein Het optionally is substituted with $C_{1-4}$ alkyl, e.g., a pyrrolidinylmethyl or piperazinylmethyl group, $C_{2-4}$alkyleneNR$^a$R$^b$, e.g., $O(CH_2)_2NMe_2$, or $NR^aR^b$, e.g., $NH_2$, NHMe and $NMe_2$. Most preferably, when A represents a pyridine group, $R^1$ represents $O(CH_2)_2NMe_2$.

$R^3$ and $R^4$ can be taken together to form a 3- or 4-membered alkylene or alkenylene chain component of a 5- or 6-membered ring containing at least one heteroatom. Preferably, $R^3$ and $R^4$ are taken together, and with the phenyl ring to which they are attached form:

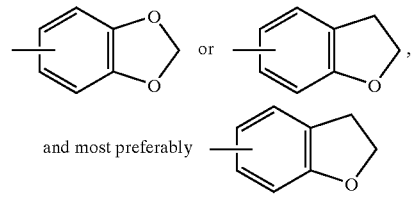

In an especially preferred subclass of compounds within the general scope of formulae (I) and (II), $R_2$ is hydrogen, n and m are the integer 1, and is represented by compounds of formula (III),

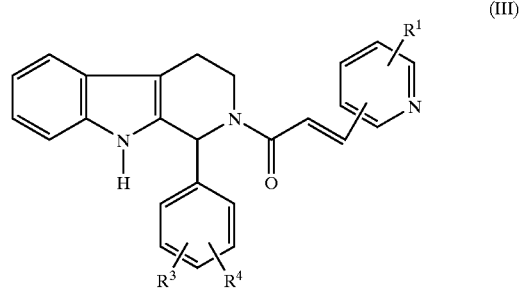

(III)

wherein
  $R^1$ is selected from the group consisting of hydrogen, a 5- or 6-membered heterocyclic group containing at least one heteroatom selected from the group consisting of oxygen, nitrogen, and sulphur, $C(=O)OR^a$, $OC_{2-4}$alkylene-NR$^1$R$^b$, and $NR^aR^b$;
  $R^3$ and $R^4$ are taken together to form a 3- or 4-membered alkylene or alkenylene chain component of a 5- or 6-membered ring, optionally containing at least one oxygen atom;
  $R^a$ and $R^b$ can be the same or different and are independently selected from hydrogen and $C_{1-6}$alkyl;
and pharmaceutically acceptable salts and solvates (e.g., hydrates) thereof.

The compounds of formula (I) can contain one asymmetric center and thus can exist as enantiomers. The present invention includes both mixtures and separate individual isomers of the compounds of formula (I).

Pharmaceutically acceptable salts of the compounds of formula (I) that contain a basic center are acid addition salts formed with pharmaceutically acceptable acids. Examples include the hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and p-toluenesulfonate salts. The compounds of the formula (I) also can provide pharmaceutically acceptable metal salts, in particular alkali metal salts, with bases. Examples include the sodium and potassium salts.

Particular individual compounds of the invention include:

(E)-1-[1-(3,4-methylenedioxyphenyl)-2,3,4,9-tetrahydro-β-carbolin-2-yl]-3-(pyridin-3-yl)-propene-1-one (E)-1-[1-(3,4-methylenedioxyphenyl)-2,3,4,9-tetrahydro-β-carbolin-2-yl]-3-(pyridin-2-yl)-propene-1-one (E)-1-[1-phenyl-2,3,4,9-tetrahydro-β-carbolin-2-yl]-3-(pyridin-2-yl)-propene-1-one (E)-1-[1-(3,4-methylenedioxyphenyl)-2,3,4,9-tetrahydro-β-carbolin-2-yl]-3-(pyridin-4-yl)-propene-1-one (E)-1-[1-(2,3-dihydrobenzofuran-5-yl)-2,3,4,9-tetrahydro-β-carbolin-2-yl]-3-3-(pyridin-3-yl)-propene-1-one (E)-1R-1-[1-(2,3-dihydrobenzofuran-5-yl)-2,3,4,9-tetrahydro-β-carbolin-2-yl]-3-[6-(2-dimethylaminoethoxy)pyridin-3-yl]-propene-1-one (E)-(R)-1-[1-(2,3-dihydrobenzofuran-5-yl)-2,3,4,9-tetrahydro-β-carbolin-2-yl]-3-(6-dimethylamino-pyridin-3-yl)-propene-1-one (E)-(R)-1-[1-(2,3-dihydrobenzofuran-5-yl)-2,3,4,9-tetrahydro-β-carbolin-2-yl]-3-(6-methylamino-pyridin-3-yl)-propene-1-one (E)-(R)-1-[1-(2,3-dihydrobenzofuran-5-yl)-2,3,4,9-tetrahydro-β-carbolin-2-yl]-3-[6-(4-methyl-piperazin-1-yl)-pyridin-3-yl]-propene-1-one (E)-(R)-1-[1-(2,3-dihydrobenzofuran-5-yl)-2,3,4,9-tetrahydro-β-carbolin-2-yl]-3-(6-pyrrolidin-1-yl-pyridin-3-yl)-propene-1-one (E)-(R)-6-{3-[1-(2,3-dihydrobenzofuran-5-yl)-2,3,4,9-tetrahydro-β-carbolin-2-yl]-3-oxo-propenyl}-nicotinic acid methyl ester (E)-(R)-6-{3-[1-(2,3-dihydrobenzofuran-5-yl)-2,3,4,9-tetrahydro-β-carbolin-2-yl]-3-oxo-propenyl}-nicotinic acid (E)-(R)-1-[1-(2,3-dihydrobenzofuran-5-yl)-2,3,4,9-tetrahydro-β-carbolin-2-yl]-3-(6-dimethylaminomethyl-pyridin-3-yl)-propene-1-one, (E)-1R-1-[1-(2,3-dihydrobenzofuran-5-yl)-2,3,4,9-tetrahydro-β-carboline-2-yl]-3-(5-dimethylaminomethyl-thiophen-2-yl)-propene-1-one, (E)-1R-1-[1-(2,3-dihydrobenzofuran-5-yl)-2,3,4,9-tetrahydro-β-carboline-2-yl]-3-(5-pyrrolidin-1-ylmethyl-thiophen-2-yl)-propene-1-one, (E)-1R-1-[1-(2,3-dihydrobenzofuran-5-yl)-2,3,4,9-tetrahydro-β-carboline-2-yl]-3-(4-methyl-piperazin-1-ylmethyl-thiophen-2-yl)-propene-1-one, (E)-1R-1-[1-(2,3-dihydrobenzofuran-5-yl)-2,3,4,9-tetrahydro-β-carboline-2-yl]-3-(5-dimethylaminomethyl-furan-2-yl)-propene-1-one, (E)-1R-1-[1[(2,3-dihydrobenzofuran-5-yl)-2,3,4,9-tetrahydro-β-carboline-2-yl]-3-(furan-2-yl)-propene-1-one, (E)-1R-1-[1[(2,3-dihydrobenzofuran-5-yl)-2,3,4,9-tetrahydro-β-carboline-2-yl]-3-(2-dimethylaminomethyl-furan-3-yl),propene-1-one, (E)-1R-1-[1[(2,3-dihydrobenzofuran-5-yl)-2,3,4,9-tetrahydro-β-carboline-2-yl]-3-(pyrimidin-5-yl)-propene-1-one, (E)-1R-1-[1[(2,3-dihydrobenzofuran-5-yl)-2,3,4,9-tetrahydro-β-carboline-2-yl]-3-(2-amino-5-pyrimidin-5-yl)-propene-1-one, (E)-1R-1-[1[(2,3-dihydrobenzofuran-5-yl)-2,3,4,9-tetrahydro-β-carboline-2-yl]-3-(pyrrolidin-1-yl)-propene-1-one, (E)-1R-1-[1[(2,3-dihydrobenzofuran-5-yl)-2,3,4,9-tetrahydro-β-carboline-2-yl]-3-(4-methyl-piperazin-1-yl)-propene-1-one, (E)-1R-1-[1[(2,3-dihydrobenzofuran-5-yl)-2,3,4,9-tetrahydro-β-carboline-2-yl]-3-(1-methyl-imidazol-4-yl)-propene-1-one, (E)-1R-1-[1[(2,3-dihydrobenzofuran-5-yl)-2,3,4,9-tetrahydro-β-carboline-2-yl]-3-(thiophen-2-yl)-propene-1-one, (E)-1R-1-[1[(2,3-dihydrobenzofuran-5-yl)-2,3,4,9-tetrahydro-β-carboline-2-yl]-3-(5-nitro-thiophen-2-yl)-propene-1-one, (E)-1R-1-[1[(2,3-dihydrobenzofuran-5-yl)-2,3,4,9-tetrahydro-β-carboline-2-yl]-3-(imidazol-4-yl)-propene-1-one, and pharmaceutically acceptable salts and solvates (e.g., hydrates) thereof.

A specific compound is:

(E)-1R-1-[1-(2,3-dihydrobenzofuran-5-yl)-2,3,4,9-tetrahydro-β-carbolin-2-yl]-3-[6-(2-dimethylaminoethoxy)pyridin-3-yl]-propene-1-one, and pharmaceutically acceptable salts and solvates (e.g., hydrates) thereof.

DETAILED DESCRIPTION OF THE PREFERRED EMBODIMENTS

It has been shown that compounds of the present invention are potent and selective inhibitors of cGMP-specific PDEs 1, 5, and 6, and particularly PDE5. Thus, compounds of formula (I) are of interest for use in therapy, specifically for the treatment of a variety of conditions where selective inhibition of PDE5 is considered to be beneficial.

In summary, the biochemical, physiological, and clinical effects of PDE5 inhibitors suggest their utility in a variety of disease states in which modulation of smooth muscle, renal, hemostatic, inflammatory, and/or endocrine function is desirable. The compounds of formula (I), therefore, have utility in the treatment of a number of disorders, including stable, unstable, and variant (Prinzmetal) angina, hypertension, pulmonary hypertension, congestive heart failure, acute respiratory distress syndrome, acute and chronic renal failure, atherosclerosis, conditions of reduced blood vessel patency (e.g., postpercutaneous transluminal coronary or carotid angioplasty, or post-bypass surgery graft stenosis), peripheral vascular disease, vascular disorders, such as Raynaud's disease, thrombocythemia, inflammatory diseases, stroke, bronchitis, chronic asthma, allergic asthma, allergic rhinitis, glaucoma, osteoporosis, preterm labor, benign prostatic hypertrophy, peptic ulcer, male and female erectile dysfunction, and diseases characterized by disorders of gut motility (e.g., irritable bowel syndrome).

An especially important use is the treatment of male erectile dysfunction, which is one form of impotence and is a common medical problem. Impotence can be defined as a lack of power, in the male, to copulate and can involve an inability to achieve penile erection or ejaculation, or both. The incidence of erectile dysfunction increases with age, with about 50% of men over the age of 40 suffering from some degree of erectile dysfunction.

Many compounds have been investigated for their therapeutic potential in the treatment of MED, including phenoxybenzamine, papaverine, prostaglandin E1 (PGE1), and phentolamine. These compounds, either alone or in combination, are typically self-administered by intracavernosal (i.c.) injection. While such treatments are effective, a treatment that is less invasive than injection therapy is preferred because pain, priapism, and fibrosis of the penis are associated with the i.c. administration of these agents.

For example, alprostadil (i.e., prostaglandin E1) delivered by intraurethral deposition has been approved for the treatment of MED. However, clinical studies showed that this route of administration is not effective in all patients. In addition, phentolamine and apomorphine are being evaluated as oral and sublingual therapies for MED, but neither compound has demonstrated efficacy across a broad range of subjects. Potassium channel openers (KCO) and vasoactive intestinal polypeptide (VIP) also have been shown to be active i.c., but cost and stability issues could limit development of the latter. An alternative to the i.c. route is the use of glyceryl trinitrate (GTN) patches applied to the penis, which has been shown to be effective but produces side effects in both patient and partner.

As an alternative to pharmacological treatment, a variety of penile prostheses have been used to assist achievement of an erection. The short-term success rate is good, but problems with infection and ischemia, especially in diabetic men, make this type of treatment a final option rather than a first-line therapy.

Because of the disadvantages of prior treatments for MED, new strategies to improve erectile response that exploit different physiological mechanisms are being investigated. One area of investigation is increasing the intracellular concentration of cGMP by providing a new type of oral therapy for the treatment of MED.

Increasing cGMP concentration is an important step in the physiology of penile erections. A penile erection is caused by neural stimuli that ultimately cause vasodilation of the arteries and sinusoidal spaces of the corpus cavernosum. Research indicates that nitric oxide plays a central role in this vasodilation.

In particular, atrial natriuretic peptides (ANP) and nitric oxide (NO, sometimes referred to as endothelium-derived relaxing factor or EDRF) relax smooth muscle by increasing guanylyl cyclase activity, which raises intracellular cGMP concentration. Intracellular cGMP is hydrolyzed by phosphodiesterases (PDEs), thereby terminating the action of the cyclic nucleotide. PDE5 is the major cGMP hydrolyzing enzyme in vascular smooth muscle. Accordingly, PDE5 inhibition potentiates the relaxant effects of ANP and nitric oxide by increasing the cGMP levels. Therefore, a compound that inhibits the PDE5 enzyme (and thereby indirectly inhibits the hydrolysis of cGMP) should potentiate the vascular response to nitric oxide, thereby facilitating the achievement and maintenance of erection.

PDE5 inhibitors have potential for use in treating male erectile dysfunction (MED), hypertension, heart failure, and other disease states because of their ability to facilitate the action of ANP and NO. For example, sildenafil, a PDE inhibitor showing little selectivity with respect to PDE6, has the structure:

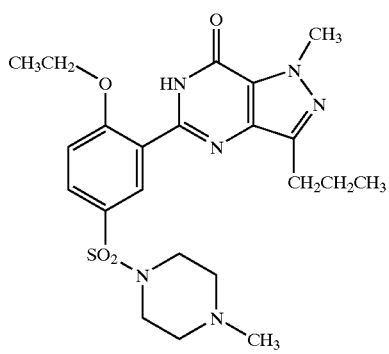

and has shown efficacy in oral administration clinical trials for MED, which support s the hypothesis that augmenting normal or subnormal guanylyl cyclase stimuli has therapeutic benefits.

It is envisioned, therefore, that compounds of formula (I) are useful in the treatment of erectile dysfunction. Furthermore, the compounds can be administered orally, thereby obviating the disadvantages associated with intracavernosal administration. Thus, the present invention concerns the use of compounds of formula (I), or a pharmaceutically acceptable salt thereof, or a pharmaceutical composition containing either entity, for the manufacture of a medicament for the curative or prophylactic treatment of erectile dysfunction in a male animal, including man.

It also has been observed that human corpus cavernosum contains three distinct PDE enzymes (see A. Taher et al., *J. Urol.*, 149, p. 285A (1993)), one of which is the cGMP-specific PDE5. As a consequence of the selective PDE5 inhibition exhibited by compounds of the present invention, the present compounds sustain cGMP levels, which in turn mediate relaxation of the corpus cavernosum tissue and consequent penile erection.

Although the compounds of the invention are envisioned primarily for the treatment of erectile dysfunction in humans, such as male erectile dysfunction and female sexual dysfunction, including orgasmic dysfunction related to clitoral disturbances, they also can be used for the treatment of premature labor and dysmenorrhea.

It is understood that references herein to treatment extend to prophylaxis, as well as treatment of established conditions.

It also is understood that "a compound of formula (I)," or a physiologically acceptable salt or solvate thereof, can be administered as the neat compound, or as a pharmaceutical composition containing either entity.

A further aspect of the present invention is providing a compound of formula (I) for use in the treat ment of stable, unstable, and variant (Prinzmetal) angina, hypertension, pulmonary hypertension, chronic obstructive pulmonary disease, congestive heart failure, acute respiratory distress syndrome, acute and chronic renal failure, atherosclerosis, conditions of reduced blood vessel patency (e.g., post-PTCA or post-bypass graft stenosis), peripheral vascular disease, vascular disorders such as Raynaud's disease, thrombocythemia, inflammatory diseases, prophylaxis of myocardial infarction, prophylaxis of stroke, stroke, bronchitis, chronic asthma, allergic asthma, allergic rhinitis, glaucoma, osteoporosis, preterm labor, benign prostatic hypertrophy, male and female erectile dysfunction, or diseases characterized by disorders of gut motility (e.g., IBS).

According to another aspect of the present invention, there is provided the use of a compound of formula (I) for the manufacture of a medicament for the treatment of the above-noted conditions and disorders.

In a further aspect, the present invention provides a method of treating the above-noted conditions and disorders in a human or nonhuman animal body which comprises administering to said body a therapeutically effective amount of a compound of formula (I).

Compounds of the invention can be administered by any suitable route, for example by oral, buccal, inhalation, sublingual, rectal, vaginal, transurethral, nasal, topical, percutaneous, i.e., transdermal, or parenteral (including intravenous, intramuscular, subcutaneous, and intracoronary) administration. Parenteral administration can be accomplished using a needle and syringe, or using a high pressure technique, like POWDERJECT™. Oral administration generally is preferred.

With respect to treating sexual dysfunction and particularly erectile dysfunction in humans, oral administration of the compounds of the invention is the preferred route. Oral administration is the most convenient and avoids the disadvantages associated with intracavernosal administration. For patients suffering from a swallowing disorder or from impairment of drug absorption after oral administration, the drug can be administered parenterally, e.g., sublingually or buccally.

For administration to man in the curative or prophylactic treatment of the conditions and disorders identified above, oral dosages of a compound of formula (I) generally are about 0.5 to about 1000 mg daily for an average adult patient (70 kg). Thus, for a typical adult patient, individual tablets or capsules contain 0.2 to 500 mg of active compound, in a suitable pharmaceutically acceptable vehicle or carrier, for administration in single or multiple doses, once or several times per day. Dosages for intravenous, buccal, or sublingual administration typically are 0.1 to 500 mg per single dose as required. In practice, the physician determines the actual dosing regimen which is most suitable for an individual patient, and the dosage varies with the age, weight, and response of the particular patient. The above dosages are exemplary of the average case, but there can be individual instances in which higher or lower dosages are merited, and such are within the scope of this invention.

For human use, a compound of the formula (I) can be administered alone, but generally is administered in admixture with a pharmaceutical carrier selected with regard to the intended route of administration and standard pharmaceutical practice. For example, the compound can be administered orally, buccally, or sublingually in the form of tablets containing excipients such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents (e.g., methylcellulose, a semisynthetic glyceride such as witepsol, or mixtures of glycerides such as a mixture of apricot kernel oil and PEG-6 esters, or mixtures of PEG-8 and caprylic/capric glycerides). A compound also can be injected parenterally, for example, intravenously, intramuscularly, subcutaneously, or intracoronarily. For parenteral administration, the compound is best used in the form of a sterile aqueous solution which can contain other substances, for example, salts, or monosaccharides, such as mannitol or glucose, to make the solution isotonic with blood.

For veterinary use, a compound of formula (I) or a nontoxic salt thereof, is administered as a suitably acceptable formulation in accordance with normal veterinary practice. The veterinarian can readily determine the dosing regimen and route of administration that is most appropriate for a particular animal.

Thus, the invention provides in a further aspect a pharmaceutical composition comprising a compound of the formula (I), together with a pharmaceutically acceptable diluent or carrier therefor.

There is further provided by the present invention a process of preparing a pharmaceutical composition comprising a compound of formula (I), which process comprises mixing a compound of formula (I), together with a pharmaceutically acceptable diluent or carrier therefor.

In a particular embodiment, the invention includes a pharmaceutical composition for the curative or prophylactic treatment of erectile dysfunction in a male animal, including man, comprising a compound of formula (I) or a pharmaceutically acceptable salt thereof, together with a pharmaceutically acceptable diluent or carrier.

A compound of formula (I) also can be used in combination with other therapeutic agents which can be useful in the treatment of the above-mentioned and other disease states. The invention thus provides, in another aspect, a combination of a compound of formula (I), together with a second therapeutically active agent.

A compound of formula (I) can be used in the preparation of a medicament for co-administration with the second therapeutically active agent in treatment of conditions where inhibition of a cGMP-specific PDE is beneficial. In addition, a compound of formula (I) can be used in the preparation of a medicament for use as adjunctive therapy with a second therapeutically active compound to treat such conditions. Appropriate doses of known second therapeutic agents for use in combination with a compound of formula (I) are readily appreciated by those skilled in the art.

In particular, because compounds of the present invention maintain cGMP levels, the compounds of formula (I) can provide beneficial antiplatelet, antineutrophil, antivasospastic, vasodilatory, natriuretic, and diuretic activities, as well as potentiate the effects of endothelium-derived relaxing factor (EDRF), gastric NO administration, nitrovasodilators, atrial natriuretic factor (ANF), brain natriuretic peptide (BNP), C-type natriuretic peptide (CNP), and endothelium-dependent relaxing agents such as bradykinin, acetylcholine, and 5-HT$_1$.

The present selective PDE5 inhibitors in combination with vasodilators, including nitric oxide and nitric oxide donators and precursors, such as the organic nitrate vasodilators which act by releasing nitric oxide in vivo, are especially useful in treatment of angina, congestive heart failure, and malignant hypertension (e.g., pheochromocytoma). Related to the capacity of the present PDE5 inhibitors to potentiate nitric oxide donors and precursors is their ability, in spontaneously hypertensive rats, to reverse the desensitization to these agents that occurs with chronic use.

Examples of vasodilators that can be used in conjunction with the compounds of formula (I) include, but are not limited to, (a) organic nitrates, such as nitroglycerin, isosorbide dinitrate, pentaerythrityl tetranitrate, isosorbide-5-mononitrate, propatyl nitrate, trolnitrate, nicroandil, mannitol hexanitrate, inositol hexanitrate, N-[3-nitratopivaloyl]-L-cysteine ethyl ester, (b) organic nitrites, like isoamyl nitrite, (c) thionitrites, (d) thionitrates, (e) S-nitrosothiols, like S-nitroso-N-acetyl-D,L-penicillamine, (f) nitrosoproteins, (g) substituted furoxanes, such as 1,2,5-oxadiazole-2-oxide and furazan-N-oxide, (h) substituted sydnonimines, such as molsidomine and mesocarb, (i) nitrosyl complex compounds, like iron nitrosyl compounds, especially sodium nitroprusside, and (j) nitric oxide (NO) itself.

Other classes of therapeutic agents that can be used in conjunction with the compounds of formula (I), in addition to vasodilators, include, but are not limited to, α-adrenergic blockers, mixed α, β-blockers, prostaglandin EI (PGEI) and prostacyclin (PGI2), angiotensin converting enzyme inhibitors (ACE inhibitors), neutral endopeptidase (NEP) inhibitors, centrally acting dopaminergic agents (such as apomorphine), vasoactive intestinal peptides (VIP), calcium channel blockers, and compounds like thiazides.

Alpha-adrenergic blockers inhibit vasoconstriction in the corpus cavernosum. Because PDE5 inhibitors enhance vasodilation of the same smooth muscle tissue, a PDE5 inhibitor of formula (I) and an α-adrenergic blocker, like phentolamine or prazocin, or a centrally acting dopaminergic agent, like apomorphine, can be expected to potentiate one another in a treatment for MED or other disorders. Potentiation of mixed α, β-blockers, like carvedilol, which is employed in treatment of hypertension, also is expected. Similarly, α₂-adrenergic blockers, like yohimbine, can be potentiated.

Prostaglandin E1 enhances relaxation of the corpus cavernosum by increasing the formation of cyclic AMP. Cyclic AMP can be degraded in the corpus cavernosum by PDE3, which is inhibited by cyclic GMP. By maintaining cyclic GMP levels, a PDE5 inhibitor can indirectly inhibit PDE3 activity, and hence block degradation of cyclic AMP. Therefore, a PDE5 inhibitor of formula (I) can be expected to potentiate the activity of PGE1 in the treatment of MED or compounds having similar activities, such as PGI2, in the treatment of pulmonary hypertension, for example.

Angiotensin converting enzyme (ACE) inhibitors block the conversion of angiotensin I into angiotensin II, which causes systemic vasoconstriction and the retention of sodium and water. PDE5 inhibitors cause vasodilation in hypertensive animals, and stimulate the excretion of sodium and water in normotensive animals. Therefore, a PDE5 inhibitor of formula (I) can be combined with an ACE inhibitor to achieve more powerful vasodilatory and natriuretic effects in, for example, treatment of congestive heart failure or hypertensive states.

Neutral endopeptidase (NEP) inhibitors inhibit the degradation of atrial natriuretic peptide (ANP) by NEP. PDE5 inhibitors can be expected to potentiate the action of ANP by inhibiting degradation of its second messenger, cyclic GMP, and, therefore, a compound of formula (I) can potentiate the effects of agents, like NEP inhibitors, that increase blood levels of ANP.

The combination referred to above can be presented for use in the form of a single pharmaceutical formulation, and, thus, pharmaceutical compositions comprising a combination as defined above together with a pharmaceutically acceptable diluent or carrier comprise a further aspect of the invention.

The individual components of such a combination, therefore, can be administered either sequentially or simultaneously from the same or separate pharmaceutical formulations. As is the case for the PDE5 inhibitors of formula (I), a second therapeutic agent can be administered by any suitable route, for example, by oral, buccal, inhalation, sublingual, rectal, vaginal, transurethral, nasal, topical, percutaneous (i.e., transdermal), or parenteral (including intravenous, intramuscular, subcutaneous, and intracoronary) administration.

In some embodiments, the compound of formula (I) and the second therapeutic agent are administered by the same route, either from the same or from different pharmaceutical compositions. However, in other embodiments, using the same route of administration for the compound of formula (I) and the second therapeutic agent either is impossible or is not preferred. For example, if the second therapeutic agent is nitric oxide, which typically is administered by inhalation, the compound of formula (I) must be administered by a different route. Furthermore, if a compound of formula (I) is used in combination with a nitrate vasodilator, for example, in treatment of an erectile dysfunction, it is preferred that the compound of formula (I) is administered orally and the vasodilator is administered topically, and preferably in a manner which avoids substantial systemic delivery of the nitrate.

The combination of a compound of formula (I) and a second therapeutic agent is envisioned in the treatment of several disease states. Examples of such treatments are the systemic and topical treatment of male and female sexual dysfunction, wherein a compound of formula (I) is used in combination with phentolamine, prazocin, apomorphine, PDE1, or a vasoactive intestinal peptide. The compound of formula (I) can be administered orally or transuretherally, and the second therapeutic agent can be administered orally, topically, or intracavernosally, for example. Persons skilled in the art are aware of the best modes of administration for each therapeutic agent, either alone or in a combination.

Other disease states that can be treated by a combination of a compound of formula (I) and a second therapeutic agent include, but are not limited to:

(a) treatment of hypertension using a compound of formula (I) in combination with an α-adrenergic blocker, a mixed α, β-blocker, like carvedilol, a thiazide, sodium nitro-prusside, an ACE inhibitor, or a calcium channel blocker;

(b) treatment of pulmonary hypertension using a compound of formula (I) in combination with inhaled NO on other inhaled vasodilators, or with PGI2 administered via an IV pump; and (c) treatment of chronic obstructive pulmonary disease using a compound of formula (I) in combination with inhaled NO.

Compounds of formula (I) can be prepared by any suitable method known in the art, or by the following processes which form part of the present invention. In the methods below, $R^0$, $R^1$, $R^2$, $R^3$, and $R^4$ are as defined in formula (I) above, unless otherwise indicated. Thus, there is a further provided by the present invention a process (A) of preparing a compound of formula (I), which process comprises reacting compounds of formulae (IV) and (V):

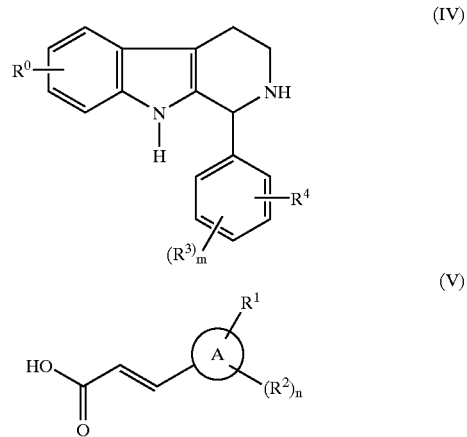

The reaction is carried out in the presence of 1-(3-dimethylaminopropyl)-3-ethylcarbodiimide hydrochloride (EDC1) and 1-hydroxybenzotriazole (HOBT) in a suitable organic solvent, such as dimethylformamide (DMF) or dichloromethane (DCM) for several hours, e.g., 8 hours to 2 days.

Compounds of formula (I) can be prepared by the method above as individual enantiomers from the appropriate enantiomer of formula (IV) or as a racemic mixture from the appropriate racemic compound of formula (IV). Individual enantiomers of the compounds of the invention can be prepared from racemates by resolution using methods known in the art for the separation of racemic mixtures into their constituent enantiomers, for example, using HPLC on a chiral column such as Hypersil naphthyl urea or using separation of salts of diastereoisomers.

A compound of formula (IV) can be prepared by Pictet-Spengler cyclization between a tryptamine derivative of formula (VI) and an aldehyde of formula (VII).

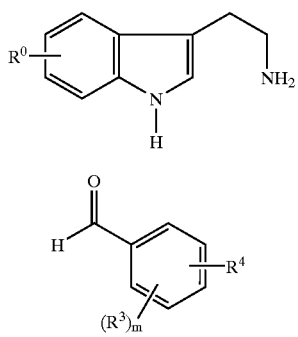

The reaction can be performed in a suitable solvent such as a halogenated hydrocarbon (e.g., dichloromethane) or an aromatic hydrocarbon (e.g., toluene) in the presence of an acid, such as trifluoroacetic acid (TFA). The reaction can be carried out at a temperature of 20° C. to reflux to provide a compound of formula (IV) in one step. The reaction also can be carried out in a solvent such as an aromatic hydrocarbon (e.g., toluene) under reflux, optionally using a Dean-Stark apparatus to trap the produced water.

The reaction provides racemic compounds of formula (IV). Enantiomers can be obtained from a resolution with N-acetyl leucine using fractional crystallization in EtOAc:MeOH (ethyl acetate:methanol) as the solvent. (R) and (S) enantiomers can be isolated as salts, depending upon whether N-acetyl-(D) and (L)-leucine was used as the starting material.

Compounds of formulae (VI) and (VII) are commercially available compounds or are prepared by standard synthetic techniques as hereinafter described in the Examples.

A compound of formula (V) can be prepared from a corresponding aldehyde of formula (VIII)

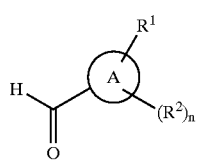

by a Knoevenagel reaction employing malonic acid, by a Wittig reaction followed by basic hydrolysis, or by a Wittig-Horner reaction.

Compounds of formula (VIII) can be prepared from known corresponding heteroaromatic carboxaldehyde or heteroaromatic nitrile derivatives, using techniques well known in the art of synthetic organic chemistry.

According to a further general process (B), compounds of formula (I) can be converted to alternative compounds of formula (I), employing suitable interconversion techniques such as hereinafter described in the Examples.

Compounds of this invention can be isolated in association with solvent molecules by crystallization from or evaporation of an appropriate solvent.

The pharmaceutically acceptable acid addition salts of the compounds of formula (I) which contain a basic center can be prepared in a conventional manner. For example, a solution of the free base can be treated with a suitable acid, either neat or in a suitable solution, and the resulting salt isolated either by filtration or by evaporation under vacuum of the reaction solvent. Pharmaceutically acceptable base addition salts can be obtained in an analogous manner by treating a solution of a compound of formula (I) with a suitable base. Both types of salt can be formed or interconverted using ion-exchange resin techniques.

Thus, according to a further aspect of the invention, a method for preparing a compound of formula (I) or a salt or solvate (e.g., hydrate) is provided, wherein the method comprises process (A) or (B) as hereinbefore described, followed by (i) salt formation, or (ii) solvate (e.g., hydrate) formation. The following additional abbreviations are used hereafter in the accompanying examples: rt (room temperature), min (minute), g (gram), mmol (millimole), m.p. (melting point), eq (equivalents), mL (milliliter), μL (microliters), DMSO (dimethyl sulfoxide), DCM (dichloromethane), TFA (trifluoracetic acid), and THF (tetrahydrofuran).

Intermediate 1

1-Phenyl-2,3,4,9-tetrahydro-1H-β-carboline

A solution of tryptamine (15 g, 94.0 mmol) and benzaldehyde (10.9 g, 1.1 eq.) in $CH_2Cl_2$ (800 mL) was treated with TFA (15 mL, 2 eq.). The resulting mixture was stirred at room temperature (rt) for one day and then neutralized to pH 7 with a saturated aqueous solution of sodium carbonate ($Na_2CO_3$). After filtration and concentration to dryness, the residue was recrystallized from 2-propanol to give the title compound (11.0 g, 47%) as white crystals (m.p.:175–177° C.).

Intermediate 2

1-(3,4-Methylenedioxyphenyl)-2,3,4,9-tetrahydro-1H-β-carboline

This compound was prepared using the same procedure as for Intermediate 1 with tryptamine (20.0 g, 120 mmol), 3,4-methylenedioxybenzaldehyde (20.6 g, 1.1 eg.) and TFA (18 mL, 2 eq.) to give the title compound (22 g, 60%) as white crystals after recrystallization from ethanol (m.p.:178° C.).

Intermediate 3

1-(2,3-Dihydrobenzofuran-5-yl)-2,3,4,9-tetrahydro-1H-β-carboline

This compound was prepared using a two-step procedure. A solution of tryptamine (32.4 g, 0.2 mol) and 2,3-dihydrobenzofuran-5-carboxaldehyde (30.0 g, 1 eq.) in toluene (1 L) was heated under reflux for 4 hours. After removal of 4 mL of water and evaporation of toluene, the residue was dissolved in $CH_2Cl_2$ (1 L) in the presence of TFA (31 mL, 2 eq.). The resulting mixture was stirred at rt for 16 hours. Then, 1 L of a saturated aqueous solution of sodium bicarbonate ($NaHCO_3$) was added. After extraction with $CH_2Cl_2$ and drying over magnesium sulfate ($MgSO_4$), the organic solution was evaporated in vacuo. Recrystallization from $CH_2Cl_2/iPr_2O$ (diisopropyl ether) (2:30) gave the title compound as white crystals in an 80% yield. $^1H$ NMR ($CDCl_3$), δ7.6 (s, 1H), 7.5–7.6 (m, 1H), 7–7.3 (m, 5H), 6.7–6.75 (d, 1H), 5.1 (s, 1H), 4.5–4.6 (t, 2H), 3.3–3.45 (m, 1H), 3.05–3.2 (t, 3H), 2.7–3 (m, 2H).

Intermediate 4

(R)-1-(2,3-Dihydrobenzofuran-5-yl)-2,3,4,9-tetrahydro-1H-β-carboline

Resolution of the corresponding racemic amine, Intermediate 3, was obtained with N-acetyl-(D)-Leucine (Sigma) in MeOH:EtOAc followed by a recrystallization from MeOH.

The suspension of the recrystallized material in CH$_2$Cl$_2$ was treated with a saturated aqueous solution of NaHCO$_3$ to give the enantiomerically pure title compound in 55% yield (m.p.:98–99° C.).

Analysis for C$_{19}$H$_{18}$N$_2$O.0.15 H$_2$O:

Calculated: C, 77.87; H, 6.29; N, 9.56

Found: C, 77.83; H, 6.33; N, 9.44 [α]$_D^{21}$=42 c=0.5, MeOH)

Intermediate 5

6-(2-Dimethylaminoethoxy)-nicotinonitrile

To a suspension of sodium hydride (NaH) 60% dispersion in mineral oil (4.5 g, 111 mmol, 1.1 eq.) in anhydrous DMF (200 mL) was added 2-dimethylaminoethanol (11.5 mL, 111 mmol. 1.1 eq.). The reaction mixture was heated to 50° C. for 30 min. Then, 6-chloronicotinonitrile (14.8 g, 101 mmol, 1 eq.) in THF (100 mL) was added dropwise and the mixture was stirred overnight at 50° C. The solvents were removed under reduced pressure, the resulting residue was dissolved in water and acidified with conc. HCl (hydrochloric acid) to pH 1. The solution was washed with CH$_2$Cl$_2$ (2×200 mL), the aqueous layer was basified with conc. NaOH (sodium hydroxide) to pH about 10 and extracted with diethyl ether. The organic phase was washed with brine, dried over Na$_2$SO$_4$, and filtered. Removal of the solvent in vacuo gave the title compound as an off-white solid (19.32 g, 99%) (m.p.:58° C.).

Intermediate 6

6-(Methylamino)-nicotinonitrile

Methylamine was bubbled into a solution of 6-chloronicotinonitrile (2 g, 14.4 mmol) in DMF (150 mL) at room temperature for 4 min. The reaction mixture was then stirred at 50° C. for 1 hour. The DMF was removed under reduced pressure. The residue was taken up in water and extracted with diethyl ether. The organic layer was washed with water and dried over Na$_2$SO$_4$. The solvent was evaporated in vacuo to give the title compound as a white solid (1.9 g, 99%). $^1$H NMR (250 MHZ, CDCl$_3$) δ(ppm):8.3 (d, 1H); 7.55 (dd, 1H); 6.35 (d, 1H); 5.4 (brd, 1H); 2.9 (d,3H).

Intermediate 7

6-(2-Dimethylaminoethoxy)-pyridine-3-carboxaldehyde

Diisobutylaluminum hydride (120 mL, 1.5 M in toluene, 1.8 eq.) was added dropwise to a solution of Intermediate 5 (19.32 g, 101 mmol) in toluene (200 mL) at −78° C. The mixture was stirred at −78° C. for 1 hour. Water (1 ml) was added, and the reaction mixture was allowed to warm to rt for 18 hours. The mixture was treated with water (60 mL), acidified with 1N HCl (pH=1), and washed with CH$_2$Cl$_2$ (3×500 mL). The combined organic layers were dried over Na$_2$SO$_4$, filtered and the solvent removed in vacuo to give the title compound as an orange oil (15.61 g, 79.6%). $^1$H NMR (250 MHZ, CDCl$_3$) δ(ppm):9.90 (s, 1H); 8.60 (d, 1H); 8 (dd, 1H); 6.85 (d, 1H); 4.50 (t, 2H); 2.70 (t, 2H); 2.30 (s, 6H).

Intermediate 8

6-(Methylamino)-pyridine-3-carboxaldehyde

The same method as described for Intermediate 7, but starting from Intermediate 6, gave the title compound as a yellow solid in an 86% yield. $^1$H NMR (250 MHZ, CDCl$_3$) δ(ppm): 9.70 (s, 1H); 8.45 (d, 1H); 7.85 (dd, 1H); 6.40 (d, 1H), 5.60 (brs, 1H); 3 (d 3H).

Intermediate 9

6-(4-Methyl-piperazin-1-yl)-pyridine-3-carboxaldehyde

The same method as described for Intermediate 7, but starting from 6-(4-methyl-piperazin-1-yl)-nicotinonitrile (prepared as described in L. Thunus, *Ann. Pharm. Fr.* (1974), 32(7–8), 443–446), gave the title compound as a yellow oil in a 56% yield. $^1$H NMR (250 MHZ, CDCl$_3$) δ(ppm): 9.70 (s, 1H); 8.50 (d, 1H); 7.85 (dd, 1H); 6.60 (d, 1H); 3.70 (t, 4H); 2.45 (t, 4H); 2.3 (s, 3H).

Intermediate 10

6-(Pyrrolidin-1-yl)-pyridine-3-carboxaldehyde

The same method as described for Intermediate 7, but starting from 6-(pyrrolidin-1-yl)-nicotinonitrile (prepared as described in R. Bernardi et al. *J. Het. Chem.* (1994), 31(4), 903–908) gave the title compound as yellow crystals in a 99% yield (m.p.:69° C.).

Intermediate 11

(E)-3-(6-(2-Dimethylaminoethyoxy-pyridin-3-yl)-acrylic Acid, Hydrochloride

A solution of Intermediate 7 (15.61 g, 80.4 mmol), malonic acid (15 g, 1.8 eq.) and piperidine (3 mL) in pyridine (200 mL) was stirred at 80° C. for 24 hours. The mixture was concentrated, the resulting residue poured into 1N NaOH and washed with CH$_2$Cl$_2$. The aqueous layer was acidified with 1N HCl and washed with CH$_2$Cl$_2$. Water was removed in vacuo to give a solid. Recrystallization of this crude material from isopropanol gave the title compound (8.3 g, 38%) as an off-white solid (m.p. (dec.):240° C.).

Intermediate 12

(E)-3-(6-Dimethylamino-Pyridin-3-yl)-acrylic Acid

The same method as described in the preparation of Intermediate 11, but starting from 6-(dimethylamino)-pyridin-3-carboxaldehyde (prepared as described in N. J. Broom et al., WO 93/06118), gave the title compound as an off-white solid in a 61% yield. $^1$H NMR (250 MHZ, DMSO) δ(ppm): 12.1 (brd, 1H); 8.30 (d, 1H); 7.90 (dd, 1H); 7.50 (d, J=15 Hz, 1H); 6.70 (d, 1H); 6.30 (d, J=15 Hz, 1H); 3.10 (s, 6H).

Intermediate 13

(E)-3-(6-Methylamino-pyridin-3-yl)-acrylic Acid

The same method as described in the preparation of Intermediate 11, but starting from Intermediate 8, gave the title compound as a yellow solid in a 50% yield.

$^1$H NMR (250 MHZ, DMSO) δ(ppm): 12.1 (brd, 1H); 8.30 (d, 1H); 7.90 (dd, 1H); 7.25 (brd, 1H); 7.60 (d, J=15 Hz, 1H); 6.60 (d, 1H); 6.35 (d, J=15 Hz, 1H); 2.95 (d, 3H).

Intermediate 14

(E)-3-(6-(4-Methylpiperazin-1-yl)-pyridin-3-yl)-acrylic Acid

The same method as described in the preparation of Intermediate 11, but starting from Intermediate 9, gave the title compound as a light yellow solid in a 90% yield. $^1$H NMR (250 MHZ, DMSO) δ(ppm) 12 (brd, 1H); 8.30 (d, 1H); 7.90 (dd, 1H); 7.50 (d, J=15 Hz, 1H); 6.90 (d, 1H); 6.35 (d, J=15 Hz, 1H); 3.60 (t, 4H); 2.40 (t, 4H); 2.20 (s, 3H).

Intermediate 15

(E)-3-(6-Pyrrolidin-1-yl-pyridin-3-yl)-acrylic Acid

The same method was employed as in the preparation of Intermediate 11, but starting from Intermediate 10, gave the title compound, after recrystallization from methanol, as light yellow crystals in a 46% yield (m.p. 170° C.)
Intermediate 16

6-(2-Carboxyvinyl)-nicotinic Acid Methyl Ester

The same method as described in the preparation of Intermediate 11, but starting from 6-formylnicotinic acid methyl ester (prepared as described in A. Markovac et al., *J. Org. Chem.* (1970), 35,3, 841–843), gave the title compound as a brown solid in a 40% yield. $^1$H NMR (250 MHZ, DMSO) δ(ppm): 9.15 (d, 1H); 8.30 (dd, 1H); 7.70 (d, J=15 Hz, 1H); 7.50 (d, 1H); 6.95 (d, J=15 Hz, 1H); 3.90 (s, 3H).
Intermediate 17

(E)-3-(6-Methylpyridin-3-yl)-acrylic Acid Methyl Ester

A mixture of 6-methylpyridine-3-carboxaldehyde (2 g, 16.5 mmol) and methyl (triphenylphosphoranylidene) acetate (6.1 g, 1.1 eq.) in toluene (100 mL) was stirred at reflux for 18 hours. The solvent was removed in vacuo, the residue washed with diethyl ether (100 mL) and filtered. The crude product was purified by chromatography eluting with $CH_2Cl_2$/MeOH (99/1) to give the title compound as a white solid (2.47 g, 85%). $^1$H NMR (CDCl$_3$, 250 MHZ) δ(ppm); 8.60 (d, 1H); 7.70 (dd, 1H); 7.65 (d, J=15 Hz, 1H); 7.20 (d, 1H); 6.50 (d, J=15 Hz, 1H); 3.85 (s, 3H); 2.60 (s, 3H).
Intermediate 18

(E)-3-(6-Formylpyridin-3-yl)-acrylic Acid Methyl Ester

A solution of Intermediate 17 (1 g, 5.6 mmol) and iodine (1.45 g, 1 eq.) in DMSO (60 mL) were heated at 150° C. After 20 minutes, a vigorous exothermic reaction and the evolution of dimethylsulfide were observed. The mixture was stirred for 40 min, cooled, neutralized with saturated aqueous NaHCO$_3$ (1L). The resulting dark suspension was extracted with diethylether, dried over Na$_2$SO$_4$, and filtered. The solvent was evaporated in vacuo to give the title compound as a brown solid (0.94 g, 88%).
$^1$H NMR (CDCl$_3$ 250 MHZ) δ(ppm): 10 (s, 1H); 8.85 (s, 1H); 7.95 (s, 1H); 7.65 (d, J=15 Hz, 1H); 6.60 (d, J=15 Hz, 1H); 3.80 (s, 3H).
Intermediate 19

(E)-3-(6-Dimethylaminomethylpyridin-3-yl)-acrylic Acid Methyl Ester

To a solution of Intermediate 18 (1.1 g, 5.75 mmol) in trimethylorthoformate (100 mL) were added acetic acid (700 μL, 2 eq.) and dimethylamine (in excess, 2.8 g). The resulting solution was stirred for 2 hours at rt, then cyanoborohydride (0.36 g, 2 eq.) was added by small portions and the mixture was stirred for 3 days at rt. The reaction mixture was poured into water, basified with 1N NaOH, and extracted with diethyl ether. The organic layer was extracted with 1N HCl. The aqueous layer was then neutralized to pH 7 and extracted with diethyl ether. The solvent was removed in vacuo to give the title compound as a yellow oil (0.84 g, 66%). $^1$H NMR (CDCl$_3$, 250 MHZ) δ(ppm): 8.55 (d, 1H); 7.80 (dd, 1H); 7.65 (d, J=15 Hz, 1H); 7.40 (d, 1H); 6.45 (d, J=15 Hz, 1H); 3.80 (s, 3H); 3.55 (s, 3H); 2.25 (s, 6H).
Intermediate 20

(E)-3-(6-Dimethylaminomethylpyridin-3-yl)-acrylic Acid

A mixture of Intermediate 19 (0.92 g, 4.18 mmol) and 1N NaOH (4.5 mL) in methanol (50 mL) was stirred at 50° C. for 18 hours. After evaporation of the solvent in vacuo, the residue was taken up in isopropyl alcohol (iPrOH) and acidified with 1N HCl (4.5 mL) to pH 6. The resulting solid was taken up in a mixture of $CH_2Cl_2$/MeOH (99/1), and filtered. The filtrate was evaporated to dryness to give the title compound (0.4 g, 46%) as a light yellow solid (m.p.:144° C.).

Intermediate 21

2-(4-Methyl-piperazin-1-ylmethyl)-thiophene

N-methyl piperazine (0.8 eq., 2.37 ml) and acetic acid (1.6 eq.), were added to trimethylorthoformate (100 ml). After 5 min., furfural (26.75 mmoles, 2.5 ml) was added, and the resulting solution was stirred for 1 hour at rt. Then, cyanoborohydride (1.1 eq., 1.8 g) was added in small portions, and the mixture was heated at 50° C. for 18 hours. After filtration, the filtrate was evaporated to dryness. The residue was taken up in 1N HCl and extracted with ether. The aqueous phase was brought to pH>10 with 1N NaOH, extracted with ether, and dried over Na$_2$SO$_4$. Evaporation in vacuo gave the title compound (4.2 g, 80%) as an oil.

EXAMPLE 1

(E)-1-[1-(3,4-Methylenedioxyphenyl)-2,3,4,9-tetrahydro-β-carbolin-2-yl]-3-(pyridin-3-yl)-propene-1-one (racemic)

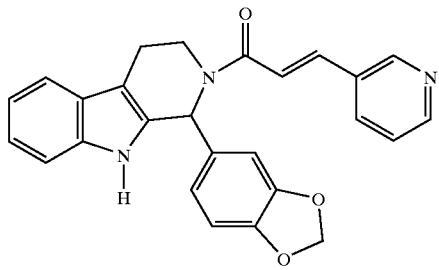

To a solution of Intermediate 2 (0.16 g, 0.55 mmol) in $CH_2Cl_2$ (70 mL) was added (E)-3-(3-pyridyl)-acrylic acid (0.09 g, 1.1 eq.), HOBT (0.08 g, 1.1 eq.), EDCl (0.11 g, 1.1 eq.), and triethylamine (Et$_3$N) (0.09 mL, 1.1 eq.). After one day of stirring at rt, the reaction was quenched with water (7 mL). The reaction mixture was extracted with $CH_2Cl_2$, then the organic layer was washed with brine and dried over Na$_2$SO$_4$. The solvent was removed in vacuo, the residue was purified by flash chromatography, eluting with $CH_2Cl_2$/MeOH (97:3). Recrystallization from ethanol gave the title compound (0.1 g, 43%) as white crystals (m.p.:240° C.).

Analysis for $C_{26}H_{21}N_3O_3$.
Calculated: C, 73.74; H, 5.00; N, 9.92;
Found: C, 73.58; H, 5.10; N, 9.80%.

EXAMPLE 2

(E)-1-[1-(3,4-Methylenedioxyphenyl)-2,3,4,9-tetrahydro-β-carbolin-2-yl]-3-(pyridin-2-yl)-propene-1-one

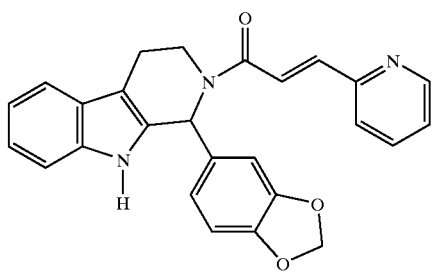

racemic

The same procedure as employed in the preparation of Example 1, but starting from (E)-3-(2-pyridyl)-acrylic acid gave the title compound (95%) as a yellow powder (m.p.: 135–141° C.).

Analysis for $C_{26}H_{21}N_3O_3.0.4H_2O$

Calculated: C, 72.51; H, 5.10; N, 9.76;

Found: C, 72.55; H, 5.06; N, 9.82%.

EXAMPLE 3

(E)-1-[1-phenyl-2,3,4,9-tetrahydro-β-carbolin-2-yl]-3-(pyridin-2-yl)-propene-1-one

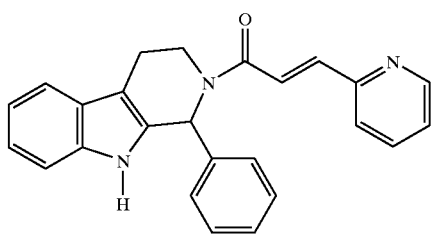

racemic

The same procedure as employed in the preparation of Example 1, but starting from Intermediate 1, and (E)-3-(2-pyridyl)-acrylic acid gave, after recrystallization from diisopropyl ether, the title compound (51%) as a white powder (m.p.:130–135° C.).

Analysis for $C_{25}H_{21}N_3O.0.7H_2O$.

Calculated: C, 76.59; H, 5.76; N, 10.72;

Found: C, 76.97; H, 6.03; N, 10.24%.

EXAMPLE 4

(E)-1-[1-(3,4-Methylenedioxyphenyl)-2,3,4,9-tetrahydro-β-carbolin-2-yl]-3-pyridin-4-yl)-propene-1-one

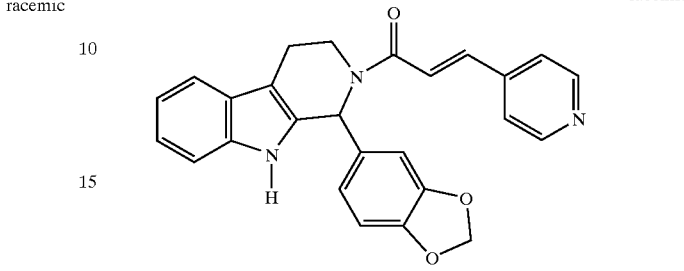

racemic

The same procedure as employed in the preparation of Example 1, but starting from (E)-3-(4-pyridyl)-acrylic acid gave, after recrystallization from ethanol, the title compound (76%) as white crystals (m.p.:224–225° C.).

Analysis for $C_{26}H_{21}N_3O_3.0.25$ EtOH.

Calculated: C, 72.97; H. 5.06; N, 9.82;

Found: C, 72.82; H, 5.03; N, 9.86%.

EXAMPLE 5

(E)-1-[1-(2,3-Dihydrobenzofuran-5-yl)-2,3,4,9-tetrahydro-β-carbolin-2-yl]-3-(pyridin-3-yl)-propene-1-one

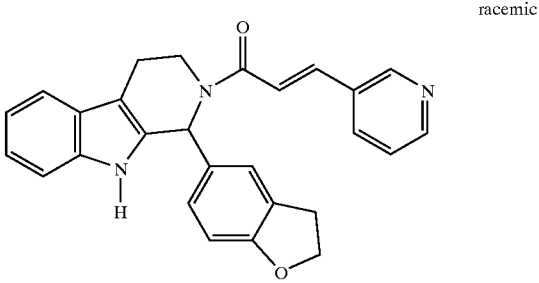

racemic

The same procedure as employed in the preparation of Example 1, but starting from Intermediate 3 and (E)-3-(3-pyridyl)-acrylic acid gave, after recrystallization from acetonitrile, the title compound (33%) as a white powder (m.p.:221–222° C.).

Analysis for $C_{27}H_{23}N_3O_2.0.45$ $CH_2Cl_2$;

Calculated: C, 71.72; H, 5.24; N, 9.14;

Found: C, 71.75, H, 5.40; N, 8.99%.

EXAMPLE 6

(E)-1R-1-[1-(2,3-Dihydrobenzofuran-5-yl)-2,3,4,9-tetrahydro-β-carbolin-2-yl]-3-[6-(2-dimethylaminoethoxy)-pyridin-3-yl]-propene-1-one

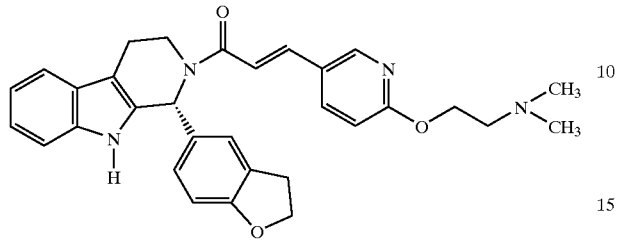

To a solution of Intermediate 4 (15.96 g, 54.97 mmol) in $CH_2Cl_2$ (100 mL) was added EDCl (21.1 g, 2 eq.), $Et_3N$ (31.5 mL, 4 eq.), HOBT (8.16 g, 1.1 eq.), and Intermediate 11 (15 g, 1 eq.). After 18 hours of stirring at rt, the reaction mixture was quenched with water (100 mL) and extracted. The organic layer was dried over $Na_2SO_4$ and evaporated to dryness under reduced pressure. The residue was purified by flash chromatography eluting with $CH_2Cl_2$ to give, after recrystallization from ethyl acetate, the title compound (18.5 g, 50%) as an off-white solid (m.p.:155° C.).

Analysis for $C_{31}H_{32}N_4O_3$;

Calculated: C, 73.21; H, 6.34; N, 11.02;

Found: C, 73.07; H, 6.57; N, 10.93%.

$[\alpha]_D^{20}=-321$ (c=0.9, $CHCl_3$).

EXAMPLE 7

(E)-(R)-1-[1-(2,3-Dihydrobenzofuran-5-yl)-2,3,4,9-tetrahydro-β-carbolin-2-yl]-3-(6-dimethylamino-pyridin-3-yl)-propene-1-one

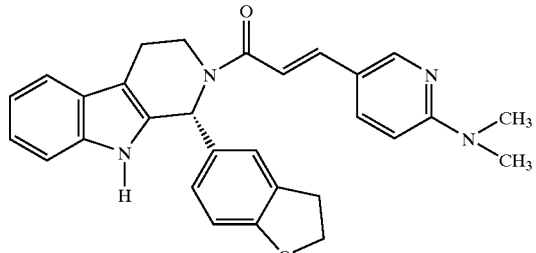

The same procedure as employed in the preparation of Example 1, but starting from Intermediate 4 and Intermediate 12, after recrystallization from acetonitrile, gave the title compound (36%) as a white solid (m.p.:171° C.).

Analysis for $C_{29}H_{28}N_4O_2 \cdot 0.3\ H_2O$;

Calculated: C, 74.11; H, 6.13; N, 11.92;

Found: C, 74.19; H, 6.23; N, 11.91%.

$[\alpha]_D^{20}=-404$ (c=1, $CHCl_3$).

EXAMPLE 8

(E)-(R)-1-[1-(2,3-Dihydrobenzofuran-5-yl)-2,3,4,9-tetrahydro-β-carbolin-2-yl]-3-(6-methylaminopyridin-3-yl)-propene-1-one

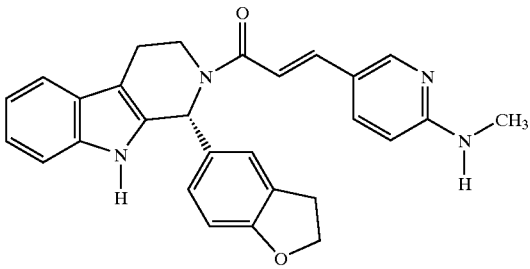

The same procedure as employed in the preparation of Example 1, but starting from Intermediate 4 and Intermediate 13, after recrystallization from methanol/water, gave the title compound (39%) as a white solid (m.p.:171° C.).

Analysis for $C_{28}H_{26}N_4O_2 \cdot 0.95\ H_2O$;

Calculated: C, 71.91; H, 6.01; N, 11.98;

Found: C, 71.68; H, 5.98; N, 11.73%.

$[\alpha]_D^{19}=-394$ (c=0.9, $CHCl_3$).

EXAMPLE 9

(E)-(R)-1-[1-(2,3-Dihydrobenzofuran-5-yl)-2,3,4,9-tetrahydro-β-carbolin-2-yl]-3-[6-(4-methylpiperazin-1-yl)-pyridin-3-yl]-propene-1-one

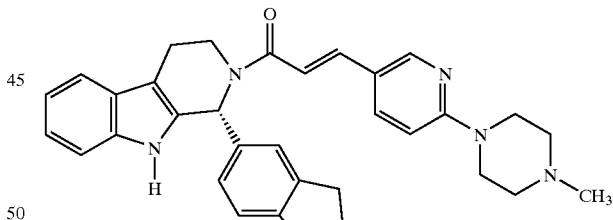

The same procedure as employed in the preparation of Example 1, but starting from Intermediate 4 and Intermediate 14, after recrystallization from diisopropyl ether, gave the title compound (54%) as a white solid (m.p.>260° C.)

Analysis for $C_{32}H_{33}N_5O_2 \cdot 0.55\ H_2O$;

Calculated: C, 72.58; H, 6,49; N, 13.22;

Found: C, 72.29; H, 6.62; N, 13.01%;

$[\alpha]_D^{20}=346$ (c=0.9, $CHCl_3$).

EXAMPLE 10

(E)-(R)-1-[1-(2,3-Dihydrobenzofuran-5-yl)-2,3,4,9-tetrahydro-β-carbolin-2-yl]-3-(6-pyrrolidin-1-yl-pyridin-3-yl)-propene-1-one

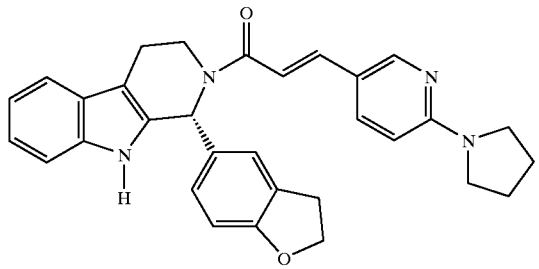

The same procedure as employed in the preparation of Example 1, but starting from Intermediate 4 and Intermediate 15, after recrystallization from acetonitrile, gave the title compound (39%) as white crystals (m.p.:201° C.)

Analysis for $C_{31}H_{30}N_4O_2.0.35\ H_2O$;

Calculated: C, 74.93; H, 6.23; N, 11.28;

Found: C, 74.83; H, 6.32; N, 11.24%.

$[\alpha]_c^{19} = -450$ (c=0.9, CHCl$_3$).

EXAMPLE 11

(E)-(R)-6-{3-[1-(2,3-Dihydrobenzofuran-5-yl)-2,3,4,9-tetrahydro-β-carbolin-2-yl]-3-oxo-propenyl}-nicotinic acid methyl ester

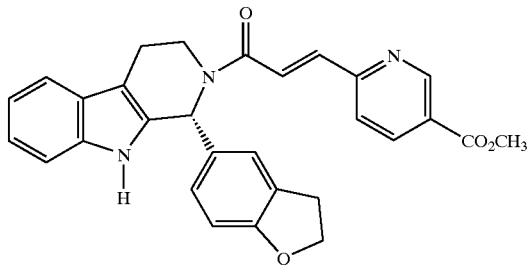

The same procedure as employed in the preparation of Example 1, but starting from Intermediate 4 and Intermediate 16, after recrystallization from acetonitrile, gave the title compound (99%) as a light yellow solid (m.p.>260° C.).

Analysis for $C_{29}H_{25}N_3O_4.0.2\ Et_2O$;

Calculated: C, 72.40; H, 5.50; N, 8.50;

Found: C, 72.30; H, 5.54; N, 8.63.

$[\alpha]_D^{20} = -349$ (c=1, CHCl$_3$).

EXAMPLE 12

(E)-(R)-6-{3-[1-(2,3-Dihydrobenzofuran-5-yl)-2,3,4,9-tetrahydro-β-carbolin-2-yl]-3-oxo-propenyl}-nicotinic acid

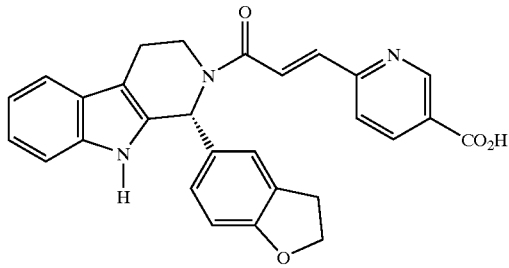

A solution of Example 11 (0.5 g, 1.04 mmol) in EtOH (50 mL) with 1N NaOH (1.1 mL, 1.1 eq.) was heated at 50° C. for 2 hours. After evaporation of the solvent in vacuo, treatment with 1N HCl (5 mL) gave a solid which was filtered. This crude product was taken up in CH$_2$Cl$_2$. After addition of pentane, a solid precipitated out, Filtration and drying in vacuo gave the title compound (33%) as a yellow solid (m.p. 183° C.).

Analysis for $C_{28}H_{23}N_3O_4.0.66H_2O$;

Calculated: C, 70.45; H, 5.13; N, 8.80;

Found: C, 70.43; H, 5.45; N, 8.85%;

$[\alpha]_D^{20} = -323$ (c=0.7, pyridine).

EXAMPLE 13

(E)-(R)-1-[1-(2,3-Dihydrobenzofuran-5-yl)-2,3,4,9-tetrahydro-β-carbolin-2-yl]-3-(6-dimethylaminomethyl-pyridin-3-yl)-propene-1-one

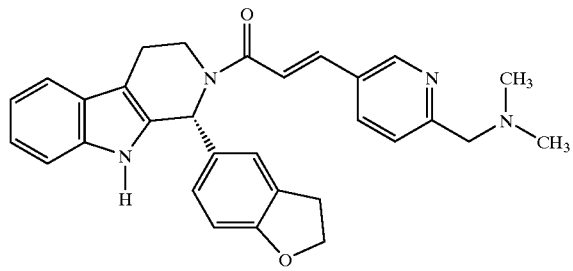

The same procedure as employed in the preparation of Example 1, but starting from Intermediate 4 and Intermediate 20, after recrystallization from acetonitrile, gave the title compound (83%) as a white solid (m.p.:163° C.)

Analysis for $C_{30}H_{30}N_4O_2.0.35\ (CH_3CN+H_2O)$;

Calculated: C, 73.86; H, 6.41; N, 12.20;

Found: C, 73.25; H, 5.82; N, 11.68%;

$[\alpha]_D^{20} = -320$ (c=1, CHCl$_3$).

The following Examples 14–27 also were prepared using the above-described procedures with starting materials that are commercially available or that can be manufactured by persons skilled in the art.

EXAMPLE 14

(E)-1R-1-[1-(2,3-Dihydrobenzofuran-5-yl)-2,3,4,9-tetrahydro-β-carbolin-2-yl]-3-(5-dimethylaminomethyl-thiophen-2-yl)-propene-1-one

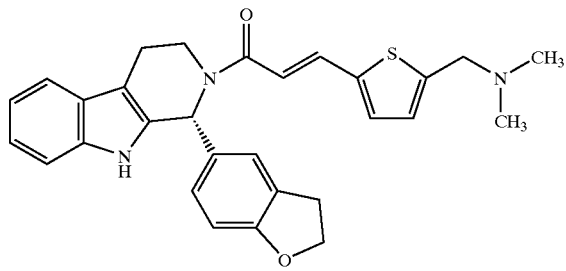

EXAMPLE 15

(E)-1R-1-[1-(2,3-Dihydrobenzofuran-5-yl)-2,3,4,9-tetrahydro-β-carbolin-2-yl]-3-(5-pyrrolidin-1-ylmethyl-thiophen-2-yl)-propene-1-one

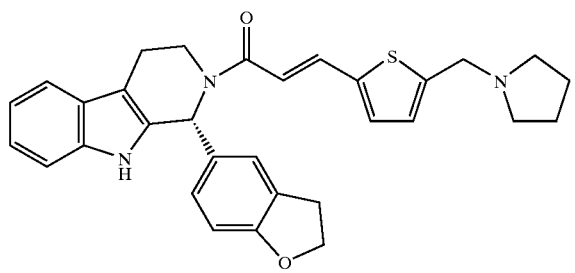

EXAMPLE 16

(E)-1R-1-[1-(2,3-Dihydrobenzofuran-5-yl)-2,3,4,9-tetrahydro-β-carbolin-2-yl]-3-(4-methyl-piperazin-1-ylmethyl-thiophen-2-yl)-propene-1-one

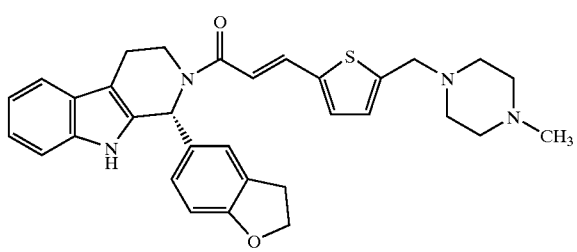

EXAMPLE 17

(E)-1R-1-[1-(2,3-Dihydrobenzofuran-5-yl)-2,3,4,9-tetrahydro-β-carbolin-2-yl]-3-(5-dimethylaminomethyl-furan-2-yl)-propene-1-one

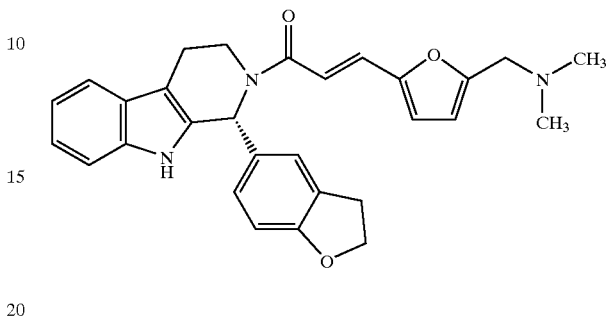

EXAMPLE 18

(E)-1R-1-[1-(2,3-Dihydrobenzofuran-5-yl)-2,3,4,9-tetrahydro-β-carbolin-2-yl]-3-(furan-2-yl)-propene-1-one

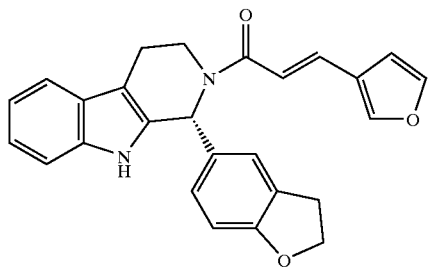

EXAMPLE 19

(E)-1R-1-[1-(2,3-Dihydrobenzofuran-5-yl)-2,3,4,9-tetrahydro-β-carbolin-2-yl]-3-(2-dimethylaminomethyl-furan-3-yl)-propene-1-one

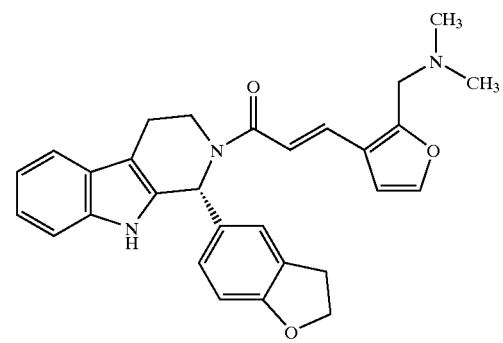

EXAMPLE 20

(E)-1R-1-[1-(2,3-Dihydrobenzofuran-5-yl)-2,3,4,9-tetrahydro-β-carboline-2-yl]-3-(pyrimidin-5-yl)-propene-1-one

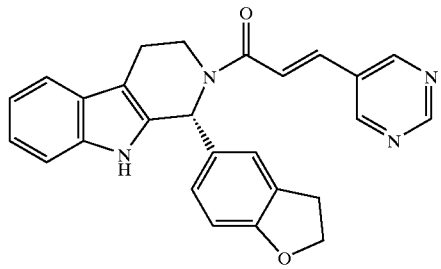

EXAMPLE 21

(E)-1R-1-[1-(2,3-Dihydrobenzofuran-5-yl)-2,3,4,9-tetrahydro-β-carboline-2-yl]-3-(2-amino-5-pyrimidin-5-yl)-propene-1-one

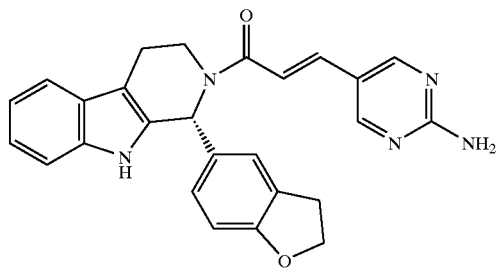

EXAMPLE 22

(E)-1R-1-[1-(2,3-Dihydrobenzofuran-5-yl)-2,3,4,9-tetrahydro-β-carboline-2-yl]-3-(pyrrolidin-1-yl)-propene-1-one

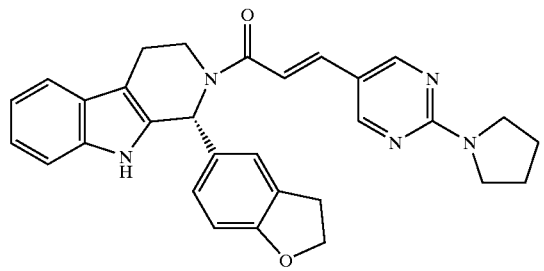

EXAMPLE 23

(E)-1R-1-[1-(2,3-Dihydrobenzofuran-5-yl)-2,3,4,9-tetrahydro-β-carboline-2-yl]-3-(4-methyl-piperazin-1-yl)-propene-1-one

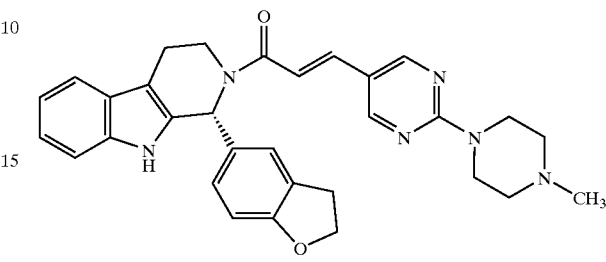

EXAMPLE 24

(E)-1R-1-[1-(2,3-Dihydrobenzofuran-5-yl)-2,3,4,9-tetrahydro-β-carboline-2-yl]-3-(1-methyl-imidazol-4-yl)-propene-1-one

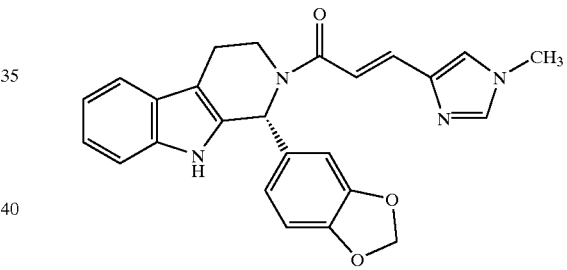

EXAMPLE 25

(E)-1R-1-[1-(2,3-Dihydrobenzofuran-5-yl)-2,3,4,9-tetrahydro-β-carboline-2-yl]-3-(thiophen-2-yl)-propene-1-one

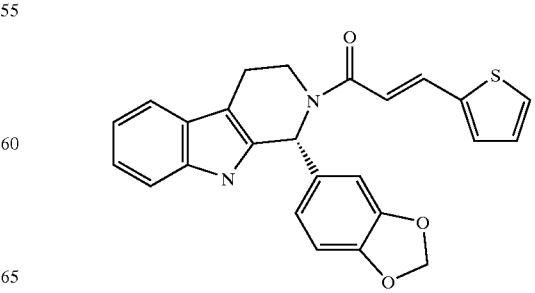

EXAMPLE 26

(E)-1R-1-[1-(2,3-Dihydrobenzofuran-5-yl)-2,3,4,9-tetrahydro-β-carboline-2-yl]-3-(5-nitro-thiophen-2-yl)-propene-1-one

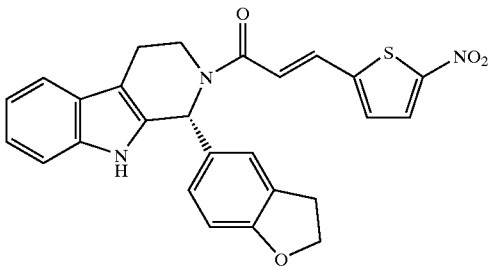

EXAMPLE 27

(E)-1R-1-[1-(2,3-Dihydrobenzofuran-5-yl)-2,3,4,9-tetrahydro-β-carboline-2-yl]-3-(imidazol-4-yl)-propene-1-one

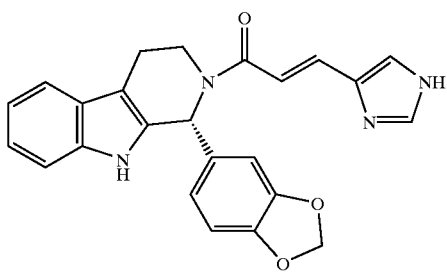

Tablets for Oral Administration

A. Direct Compression

| 1. | mg/tablet |
|---|---|
| Active ingredient | 50.0 |
| Crospovidone USNF | 8.0 |
| Magnesium Stearate Ph Eur | 1.0 |
| Anhydrous Lactose | 141.0 |

The active ingredient was sieved and blended with the excipients. The resultant mix was compressed into tablets.

| 2. | mg/tablet |
|---|---|
| Active ingredient | 50.0 |
| Colloidal Silicon Dioxide | 0.5 |
| Crospovidone | 8.0 |
| Sodium Lauryl Sulfate | 1.0 |
| Magnesium Stearate Ph Eur | 1.0 |
| Microcrystalline Cellulose USNF | 139.5 |

The active ingredient was sieved and blended with the excipients. The resultant mix was compressed into tablets.

B. Wet Granulation

| 1. | mg/tablet |
|---|---|
| Active ingredient | 50.0 |
| Polyvinylpyrrolidone | 150.0 |
| Polyethylene glycol | 50.0 |
| Polysorbate 80 | 10.0 |
| Magnesium Stearate Ph Eur | 2.5 |
| Croscarmellose Sodium | 25.0 |
| Colloidal Silicon Dioxide | 2.5 |
| Microcrystalline Cellulose USNF | 210.0 |

The polyvinyl pyrollidone, polyethylene glycol, and polysorbate 80 were dissolved in water. The resultant solution was used to granulate the active ingredient. After drying, the granules were screened, then extruded at elevated temperatures and pressures. The extrudate was milled and/or screened, then was blended with the microcrystalline cellulose, croscarmellose sodium, colloidal silicon dioxide, and magnesium stearate. The resultant mix was compressed into tablets.

| 2. | mg/tablet |
|---|---|
| Active ingredient | 50.0 |
| Polysorbate 80 | 3.0 |
| Lactose Ph Eur | 178.0 |
| Starch BP | 45.0 |
| Pregelatinized Maize Starch BP | 22.5 |
| Magnesium Stearate BP | 1.5 |

The active ingredient was sieved and blended with the lactose, starch, and pregelatinized maize starch. The polysorbate 80 was dissolved in purified water. Suitable volumes of the polysorbate 80 solution were added and the powders were granulated. After drying, the granules were screened and blended with the magnesium stearate. The granules were then compressed into tablets.

Tablets of other strengths can be prepared by altering the ratio of active ingredient to the other excipients.

Film Coated Tablets

The aforementioned tablet formulations were film coated.

| Coating Suspension | % w/w |
|---|---|
| Opadry white † | 13.2 |
| Purified water Ph Eur | to 100.0* |

*The water did not appear in the final product. The maximum theoretical weight of solids applied during coating was 20 mg/tablet.

The tablets were film coated using the coating suspension in conventional film coating equipment.

Capsules

| 1. | mg/capsule |
|---|---|
| Active ingredient | 50.0 |
| Lactose | 148.5 |
| Polyvinylpyrrolidone | 100.0 |
| Magnesium Stearate | 1.5 |

The active ingredient was sieved and blended with the excipients. The mix was filled into size No. 1 hard gelatin capsules using suitable equipment.

| 2. | mg/capsule |
|---|---|
| Active ingredient | 50.0 |
| Microcrystalline Cellulose | 233.5 |
| Sodium Lauryl Sulphate | 3.0 |
| Crospovidone | 12.0 |
| Magnesium Stearate | 1.5 |

The active ingredient was sieved and blended with the excipients. The mix was filled into size No. 1 hard gelatin capsules using suitable equipment.

Other doses can be prepared by altering the ratio of active ingredient to excipient, the fill weight, and, if necessary, changing the capsule size.

| 3. | mg/capsule |
|---|---|
| Active ingredient | 50.0 |
| Labrafil M1944CS | to 1.0 ml |

The active ingredient was sieved and blended with the Labrafil. The suspension was filled into soft gelatin capsules using appropriate equipment.

Inhibitory Effect on cGMP-PDE cGMP-PDE activity of compounds of the present invention was measured using a one-step assay adapted from Wells et al., *Biochim. Biophys. Acta,* 384, 430 (1975). The reaction medium contained 50 mM Tris-HCl, pH 7.5, 5 mM magnesium acetate, 250 μg/ml 5'-Nucleotidase, 1 mM EGTA, and 0.15 μM 8-[$H^3$]-cGMP. The enzyme used was a human recombinant PDE5 (ICOS Corp., Bothell, Wash.).

Compounds of the invention were dissolved in DMSO finally present at 2% in the assay. The incubation time was 30 minutes during which the total substrate conversion did not exceed 30%.

The $IC_{50}$ values for the compounds examined were determined from concentration-response curves typically using concentrations ranging from 10 nM to 10 μM. Tests against other PDE enzymes using standard methodology also showed that compounds of the invention are highly selective for the cGMP-specific PDE enzyme.

cGMP Level Measurements

Rat aortic smooth muscle cells (RSMC), prepared according to Chamley et al., *Cell Tissue Res.,* 177, 503–522 (1977), were used between the 10th and 25th passage at confluence in 24-well culture dishes. Culture media was aspirated and replaced with PBS (0.5 ml) containing the compound tested at the appropriate concentration. After 30 minutes at 37° C., particulates guanylate cyclase was stimulated by addition of ANF (100 nM) for 10 minutes. At the end of incubation, the medium was withdrawn, and two extractions were performed by addition of 65% ethanol (0.25 ml). The two ethanolic extracts were pooled and evaporated until dryness, using a Speed-vac system. cGMP was measured after acetylation by scintillation proximity immunoassay (AMERSHAM). The $EC_{50}$ values are expressed as the dose-giving half of the stimulation at saturating concentrations.

Biological Data

The compounds according to the present invention were typically found to exhibit an $IC_{50}$ value of less than 500 nM and an $EC_{50}$ value of less than 5 μM. In vitro test data for representative compounds of the invention is given in the following table:

TABLE 1

In vitro results

| Example | PDE5 $IC_{50}$ (nM) | RSMC $EC_{50}$ (μM) |
|---|---|---|
| 1 | 58 | 0.5 |
| 2 | 76 | |
| 3 | 740 | |
| 4 | 46 | 0.5 |
| 5 | 14 | <1 |
| 6 | 10 | <1 |
| 7 | 6 | <1 |
| 8 | 7 | <1 |
| 9 | 25 | 1 |
| 10 | 9 | <1 |
| 11 | 27 | <1 |
| 12 | 3 | 5 |
| 13 | 30 | <1 |
| 14 | 5 | 1.5 |
| 15 | 40 | 1.5 |
| 16 | 4 | 3.5 |
| 17 | 20 | <1 |
| 18 | <10 | <1 |
| 19 | 40 | 4 |
| 20 | 40 | <1 |
| 21 | 7 | <<1 |
| 22 | 6 | <1 |
| 23 | 8 | <1 |
| 24 | 126 | <1 |
| 25 | 69 | 0.5 |
| 26 | 40 | <1 |
| 27 | 80 | 1.8 |

The hypotensive effects of compounds according to the invention as identified in Table 2 were studied in conscious spontaneously hypertensive rats (SHRs). The compounds were administered orally at a dose of 5 mg/kg in a mixture of 5% DMF and 95% olive oil. Blood pressure was measured from a catheter inserted in the carotid artery and recorded for five hours after administration. The results are expressed as Area Under the Curve (AUC) from 0 to 5 hours, mm Hg.hours of the fall in blood pressure over time.

TABLE 2

In vivo results

| Example No. | SHR AUC PO (mm Hg.h) |
|---|---|
| 1 | 61 |
| 5 | 12 |
| 6 | 95 |
| 7 | 156 |
| 8 | 50 |
| 9 | 63 |
| 13 | 57 |
| 14 | 107 |
| 15 | 96 |
| 17 | 40 |
| 18 | 41 |
| 20 | 48 |
| 21 | 124 |
| 22 | 9 |
| 23 | 108 |

Obviously, many modifications and variations of the invention as hereinbefore set forth can be made without departing from the spirit and scope thereof, and, therefore, only such limitations should be imposed as are indicated by the appended claims.

What is claimed is:
1. A compound represented by a formula

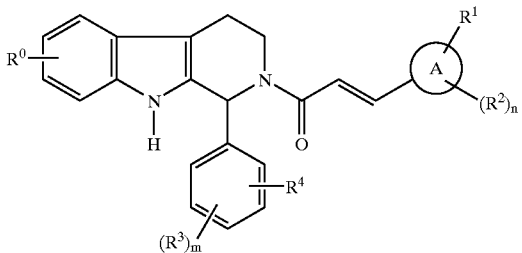

wherein
A represents a 5- or 6-membered heteroaryl group containing at least one heteroatom selected from the group consisting of oxygen, nitrogen, and sulphur;
$R^0$ represents hydrogen or halogen;
$R^1$ is selected from the group consisting of
hydrogen,
nitro,
trifluoromethyl,
trifluoromethoxy,
halogen,
cyano,
a 5- or 6-membered heterocyclic group containing at least one heteroatom selected from the group consisting of oxygen, nitrogen, and sulphur, optionally substituted with $C(=O)OR^a$ or $C_{1-4}$alkyl,
$C_{1-6}$alkyl, optionally substituted with $OR^a$,
$C_{1-3}$alkoxy,
$C(=O)R^a$,
$O-C(=O)R^a$,
$C(=O)OR^a$,
$C_{1-4}$alkyleneHet,
$C_{1-4}$alkylene $C(=O)OR^a$,
$O-C_{1-4}$alkylene-$C(=O)OR^a$,
$C_{1-4}$alkylene-$O-C_{1-4}$alkylene-$C(=O)OR^a$,
$C(=O)NR^aSO_2R^c$,
$C(=O)C_{1-4}$alkyleneHet,
$C_{1-4}$alkylene $NR^aR^b$,
$C_{2-6}$alkenyleneNR$^a$R$^b$,
$C(=O)NR^aR^b$,
$C(=O)NR^aR^c$,
$C(=O)NR^aC_{1-4}$alkylene $OR^b$,
$C(=O)NR^aC_{1-4}$alkyleneHet,
$OR^a$,
$OC_{2-4}$alkylene $NR^aR^b$,
$OC_{1-4}$alkylene-CH $(OR^a)CH_2$ $NR^aR^b$,
$O-C_{1-4}$alkyleneHet,
$O-C_{2-4}$alkylene-$OR^a$,
$O-C_{2-4}$alkylene-$NR^a-C(=O)-OR^b$,
$NR^aR^b$,
$NR^aC_{1-4}$alkyleneNR$^a$R$^b$,
$NR^1C(=O)R^b$,
$NR^1C(=O)NR^aR^b$,
$N(SO_2C_{1-4}$alkyl$)_2$,
$NR^a(SO_2C_{1-4}$alkyl$)$,
$SO_2NR^aR^b$,
and $OSO_2$trifluoromethyl;
$R^2$ is selected from the group consisting of hydrogen, halogen, $OR^a$, $C_{1-6}$alkyl, nitro, and $NR^aR^b$;
or $R^1$ and $R^2$ are taken together to form a 3- or 4-membered alkylene or alkenylene chain, optionally containing at least one heteroatom component of a 5- or 6-membered ring;

$R^3$ is selected from the group consisting of hydrogen, halogen, $NO_2$, trifluoromethoxy, $C_{1-6}$alkyl, $OC_{1-6}$alkyl, and $C(=O)OR^a$;
$R^4$ is hydrogen,
or $R^3$ and $R^4$ are taken together to form a 3- or 4-membered alkylene or alkenylene chain component of a 5- or 6-membered ring, optionally containing at least one heteroatom;
Het represents a 5- or 6-membered heterocyclic group containing at least one heteroatom selected from the group consisting of oxygen, nitrogen, and sulfur, and is optionally substituted with $C_{1-4}$alkyl;
$R^a$ and $R^b$ can be the same or different, and are independently selected from hydrogen and $C_{1-6}$alkyl;
$R^c$ represents phenyl or $C_{4-6}$cycloalkyl, wherein the phenyl or $C_{4-6}$cycloalkyl can be optionally substituted with one or more halogen atoms, one or more $C(=O)OR^a$, or one or more $OR^a$;
n is an integer 1, 2, or 3;
m is an integer 1 or 2;
or a pharmaceutically acceptable salt or solvate thereof.
2. The compound of claim 1 represented by the formula

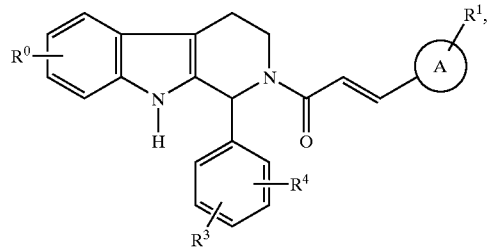

wherein
$R^1$ is selected from the group consisting of
hydrogen,
nitro,
halogen,
cyano,
a 5- or 6-membered heterocyclic group containing at least one heteroatom selected from the group consisting of oxygen, nitrogen, and sulphur, optionally substituted with $C(=O)OR^a$ or $C_{1-4}$alkyl,
$C_{1-6}$alkyl optionally substituted with $OR^1$,
$C_{1-3}$alkoxy,
$C(=O)OR^a$,
$C_{1-4}$alkyleneHet,
$O-C_{1-4}$alkylene-$C(=O)OR^a$,
$C_{1-4}$alkyleneNR$^a$R$^b$,
$C(=O)NR^aR^b$,
$C(=O)NR^aR^c$,
$OR^a$,
$OC_{2-4}$alkyleneNR$^a$R$^b$,
$O-C_{1-4}$alkyleneHet,
$NR^aR^b$,
and $NR^aC_{1-4}$alkyleneNR$^a$R$^b$;
$R^2$ is hydrogen;
n is the integer 1; and
m is the integer 1.
3. The compound of claim 1 wherein A is selected from the group consisting of thiophenyl, furyl, pyrrolyl, imidazolyl, pyrimidinyl, and pyridyl.
4. The compound of claim 3 wherein A is pyridyl.
5. The compound of claim 3 wherein when A is thiophenyl, $R^1$ is selected from the group consisting of hydrogen, nitro, $C_{1-4}$alkylene $NR^aR^b$, and $C_{1-4}$alkyleneHet.

6. The compound of claim 3 wherein when A is furyl, $R^1$ is hydrogen or $C_{1-4}$alkyleneNR$^a$R$^b$.

7. The compound of claim 3 wherein when A is pyrimidinyl, $R^1$ is hydrogen or $NH_2$.

8. The compound of claim 3 wherein when A is pyridyl, $R^1$ is selected from the group consisting of hydrogen, C(=O)OR$^a$, $C_{1-4}$alkyleneeHet, $C_{1-4}$alkyleneNR$^a$R$^b$, $OC_{2-4}$alkyleneNR$^a$R$^b$, and NR$^a$R$^b$, and a 5- or 6-membered heterocyclic group containing at least one heteroatom selected from the group consisting of oxygen, nitrogen, and sulphur, optionally substituted with $C_{1-4}$alkyl.

9. The compound of claim 8 wherein $R^1$ is selected from the group consisting of $O(CH_2)_2NMe_2$, N-methyl imidazolyl, N-methyl piperazinyl, pyrrolidinyl, $CO_2H$, $CO_2Me$, a pyrrolidinylmethyl, a piperazinylmethyl, $NH_2$, NHMe, and $NMe_2$.

10. The compound of claim 1 wherein $R^3$ and $R^4$ are taken together to form a 3- or 4-membered alkylene or alkenylene chain component of a 5- or 6-membered ring containing at least one heteroatom.

11. The compound of claim 10 wherein $R^3$ and $R^4$ are taken together, and with the phenyl ring to which $R^3$ and $R^4$ are attached, form

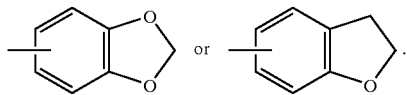

12. The compound of claim 2 corresponding to the formula

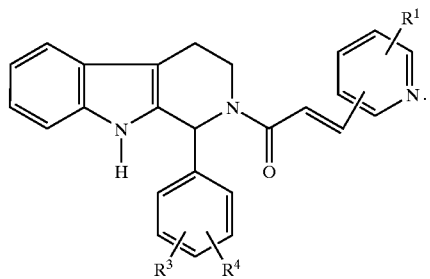

13. A compound selected from the group consisting of (E)-1-[1-(3,4-methylenedioxyphenyl)-2,3,4,9-tetrahydro-β-carbolin-2-yl]-3-(pyridin-3-yl)-propene-1-one, (E)-1-[1-(3,4-methylenedioxyphenyl)-2,3,4,9-tetrahydro-β-carbolin-2-yl]-3-(pyridin-2-yl)-propene-1-one, (E)-1-[1-phenyl-2,3,4,9-tetrahydro-β-carbolin-2-yl]-3-(pyridin-2-yl)-propene-1-one, (E)-1-[1-(3,4-methylenedioxyphenyl)-2,3,4,9-tetrahydro-β-carbolin-2-yl]-3-(pyridin-4-yl)-propene-1-one, (E)-1-[1-(2,3-dihydrobenzofuran-5-yl)-2,3,4,9-tetrahydro-β-carbolin-2-yl]-3-(pyridin-3-yl)-propene-1-one, (E)-1R-1-[1-(2,3-dihydrobenzofuran-5-yl)-2,3,4,9-tetrahydro-β-carbolin-2-yl]-3-[6-(2-dimethylaminoethoxy)pyridin-3-yl]-propene-1-one, (E)-(R)-1-[1-(2,3-dihydrobenzofuran-5-yl)-2,3,4,9-tetrahydro-β-carbolin-2-yl]-3-(6-dimethylamino-pyridin-3-yl)-propene-1-one, (E)-(R)-1-[1-(2,3-dihydrobenzofuran-5-yl)-2,3,4,9-tetrahydro-β-carbolin-2-yl]-3-(6-methylamino-pyridin-3-yl)-propene-1-one, (E)-(R)-1-[1-(2,3-dihydrobenzofuran-5-yl)-2,3,4,9-tetrahydro-β-carbolin-2-yl]-3-[6-(4-methyl-piperazin-1-yl)-pyridin-3-yl]-propene-1-one, (E)-(R)-1-[1-(2,3-dihydrobenzofuran-5-yl)-2,3,4,9-tetrahydro-β-carbolin-2-yl]-3-(6-pyrrolidin-1-yl-pyridin-3-yl)-propene-1-one, (E)-(R)-6-{3-[1-(2,3-dihydrobenzofuran-5-yl)-2,3,4,9-tetrahydro-β-carbolin-2-yl]-3-oxo-propenyl}-nicotinic acid methyl ester, (E)-(R)-6-{3-[1-(2,3-dihydrobenzofuran-5-yl)-2,3,4,9-tetrahydro-β-carbolin-2-yl]-3-oxo-propenyl}-nicotinic acid, (E)-(R)-1-[1-(2,3-dihydrobenzofuran-5-yl)-2,3,4,9-tetrahydro-β-carbolin-2-yl]-3-(6-dimethylamino-methyl-pyridin-3-yl)-propene-1-one, (E)-1R-1-[1-(2,3-dihydrobenzofuran-5-yl)-2,3,4,9-tetrahydro-β-carboline-2-yl]-3-(5-dimethyl-aminomethyl-thiophen-2-yl)-propene-1-one, (E)-1R-1-[1-(2,3-dihydrobenzofuran-5-yl)-2,3,4,9-tetrahydro-β-carboline-2-yl]-3-(5-pyrrolidin-1-ylmethyl-thiophen-2-yl)-propene-1-one, (E)-1R-1-[1-(2,3-dihydrobenzofuran-5-yl)-2,3,4,9-tetrahydro-β-carboline-2-yl]-3-(4-methyl-piperazin-1-ylmethyl-thiophen-2-yl)-propene-1-one, (E)-1R-1-[1-(2,3-dihydrobenzofuran-5-yl)-2,3,4,9-tetrahydro-β-carboline-2-yl]-3-(5-dimethyl-aminomethyl-furan-2-yl)-propene-1-one, (E)-1R-1-[1[(2,3-dihydrobenzofuran-5-yl)-2,3,4,9-tetrahydro-β-carboline-2-yl]-3-(furan-2-yl)-propene-1-one, (E)-1R-1-[1[(2,3-dihydrobenzofuran-5-yl)-2,3,4,9-tetrahydro-β-carboline-2-yl]-3-(2-dimethyl-aminomethyl-furan-3-yl),propene-1-one, (E)-1R-1-[1[(2,3-dihydrobenzofuran-5-yl)-2,3,4,9-tetrahydro-β-carboline-2-yl]-3-(pyrimidin-5-yl)-propene-1-one, (E)-1R-1-[1[(2,3-dihydrobenzofuran-5-yl)-2,3,4,9-tetrahydro-β-carboline-2-yl]-3-(2-amino-5-pyrimidin-5-yl)-propene-1-one, (E)-1R-1-[1[(2,3-dihydrobenzofuran-5-yl)-2,3,4,9-tetrahydro-β-carboline-2-yl]-3-(pyrrolidin-1-yl)-propene-1-one, (E)-1R-1-[1[(2,3-dihydrobenzofuran-5-yl)-2,3,4,9-tetrahydro-β-carboline-2-yl]-3-(4-methyl-piperazin-1-yl)-propene-1-one, (E)-1R-1-[1[(2,3-dihydrobenzofuran-5-yl)-2,3,4,9-tetrahydro-β-carboline-2-yl]-3-(1-methyl-imidazol-4-yl)-propene-1-one, (E)-1R-1-[1[(2,3-dihydrobenzofuran-5-yl)-2,3,4,9-tetrahydro-β-carboline-2-yl]-3-(thiophen-2-yl)-propene-1-one, (E)-1R-1-[1[(2,3-dihydrobenzofuran-5-yl)-2,3,4,9-tetrahydro-β-carboline-2-yl]-3-(5-nitro-thiophen-2-yl)-propene-1-one, (E)-1R-1-[1[(2,3-dihydrobenzofuran-5-yl)-2,3,4,9-tetrahydro-β-carboline-2-yl]-3-(imidazol-4-yl)-propene-1-one, and a pharmaceutically acceptable salt or solvate thereof.

14. (E)-1R-1-[1-(2,3-dihydrobenzofuran-5-yl)-2,3,4,9-tetrahydro-β-carbolin-2-yl]-3-[6-(2-dimethylaminoethoxy)pyridin-3-yl]-propene-1-one, or a pharmaceutically acceptable salt or solvate thereof.

15. A pharmaceutical composition comprising a compound of claim 1, together with a pharmaceutically acceptable diluent or carrier.

16. A method of treating a male or female animal in the treatment of a condition where inhibition of a cGMP-specific PDE is of a therapeutic benefit comprising treating said animal with an effective amount of a pharmaceutical composition comprising a compound of claim 1, together with a pharmaceutically acceptable diluent or carrier.

17. The method of claim 16 wherein the condition is erectile dysfunction.

18. A method of treating a condition where inhibition of a cGMP-specific PDE is of therapeutic benefit, in a human or a nonhuman animal body, comprising administering to said body a therapeutically effective amount of a compound of claim 1.

19. The method of claim 18 wherein the condition is erectile dysfunction in a male or female animal.

20. The method of claim 19 wherein the treatment is an oral treatment.

21. The method of claim 18 wherein the condition is selected from the group consisting of stable angina, unstable angina, variant angina, hypertension, pulmonary hypertension, chronic obstructive pulmonary disease, malignant hypertension, pheochromocytoma, acute respiratory distress syndrome, congestive heart failure, acute renal failure, chronic renal failure, atherosclerosis, a condition of reduced blood vessel patency, a vascular disorder, thrombocythemia, an inflammatory disease, myocardial infarction, stroke, bronchitis, chronic asthma, allergic asthma, allergic rhinitis, glaucoma, peptic ulcer, a gut motility disorder, postpercutaneous transluminal coronary angioplasty, carotid angioplasty, post-bypass surgery graft stenosis, osteoporosis, preterm labor, benign prostatic hypertrophy, and irritable bowel syndrome.

22. A process for preparing a compound of claim 1 comprising interacting a compound of formula (IV)

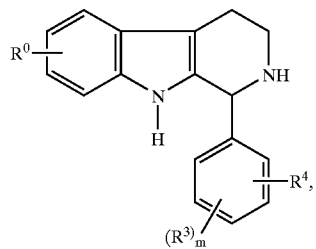

with a compound of formula (V)

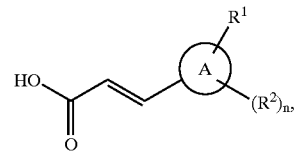

optionally followed by an interconversion step and/or solvate formation.

* * * * *

UNITED STATES PATENT AND TRADEMARK OFFICE
CERTIFICATE OF CORRECTION

PATENT NO. : 6,462,047 B1
DATED : October 8, 2002
INVENTOR(S) : Agnes Bombrun et al.

It is certified that error appears in the above-identified patent and that said Letters Patent is hereby corrected as shown below:

Column 5,
Line 11, "β-carbolin-2-yl]-3-3-(pyridin-3-yl)" should be
-- β-carbolin-2-yl]-3-(pyridin-3-yl --

Column 7,
Line 65, "support s" should be -- supports --

Column 8,
Line 33, "treat ment" should be -- treatment --

Column 16,
Lines 23, 35, 45, 55 and 65, "Acid" should be -- acid --

Column 17,
Line 5, "Acid Methyl Ester" should be -- acid methyl ester --
Lines 14 and 15, "Acid Methyl Ester" should be -- acid methyl ester --

Signed and Sealed this

Fourth Day of March, 2003

JAMES E. ROGAN
*Director of the United States Patent and Trademark Office*